United States Patent
Bonutti et al.

(10) Patent No.: US 8,206,329 B2
(45) Date of Patent: Jun. 26, 2012

(54) RANGE OF MOTION DEVICE

(75) Inventors: Boris P. Bonutti, Effingham, IL (US);
Peter M. Bonutti, Effingham, IL (US);
Kevin R. Ruholl, Effingham, IL (US);
Glen A. Phillips, Effingham, IL (US)

(73) Assignee: Bonutti Research, Inc., Effingham, IL (US)

(*) Notice: Subject to any disclaimer, the term of this patent is extended or adjusted under 35 U.S.C. 154(b) by 1 day.

(21) Appl. No.: 13/151,962

(22) Filed: Jun. 2, 2011

(65) Prior Publication Data
US 2011/0230801 A1 Sep. 22, 2011

Related U.S. Application Data

(63) Continuation of application No. 12/272,436, filed on Nov. 17, 2008, now Pat. No. 7,981,067, which is a continuation of application No. 11/533,839, filed on Sep. 21, 2006, now Pat. No. 7,452,342, which is a continuation-in-part of application No. 10/795,892, filed on Mar. 8, 2004, now Pat. No. 7,112,179, and a continuation-in-part of application No. 11/261,424, filed on Oct. 28, 2005, now Pat. No. 8,066,656.

(51) Int. Cl.
*A61F 5/00* (2006.01)

(52) U.S. Cl. .................. 602/16; 602/20; 602/23
(58) Field of Classification Search ............. 602/5, 16, 602/20–30; 128/878–879, 882
See application file for complete search history.

(56) References Cited

U.S. PATENT DOCUMENTS

| | | | | |
|---|---|---|---|---|
| 5,167,612 A | * | 12/1992 | Bonutti | 602/20 |
| 5,285,773 A | * | 2/1994 | Bonutti et al. | 601/34 |
| 5,365,947 A | * | 11/1994 | Bonutti | 128/898 |
| 5,456,268 A | * | 10/1995 | Bonutti | 128/898 |

* cited by examiner

*Primary Examiner* — Michael A. Brown
(74) *Attorney, Agent, or Firm* — Armstrong Teasdale LLP

(57) ABSTRACT

The present provides an orthosis for stretching tissue around a joint of a patient between first and second relatively pivotable body portions. The orthosis includes a first arm member affixable to the first body portion and including a first extension member extending therefrom. A second arm member affixable to the second body portion is also included and has a second extension member having an arcuate shape extending therefrom. The second extension member is operatively connected to the first extension member and travels through the first extension member along an arcuate path when the second arm member is moved from a first position to a second position relative to the first arm member.

18 Claims, 30 Drawing Sheets

RANGE OF MOTION DEVICE

CROSS-REFERENCE TO RELATED APPLICATIONS

This patent application is a continuation application of U.S. patent application Ser. No. 12/272,436 filed on Nov. 17, 2008, now U.S. Pat. No. 7,981,067 which is a Continuation of U.S. patent application Ser. No. 11/533,839 filed on Sep. 21, 2006, now U.S. Pat. No. 7,452,342 which is a Continuation-In-Part of U.S. patent application Ser. No. 10/795,892 filed on Mar. 8, 2004 now U.S. Pat. No. 7,112,179. U.S. patent application Ser. No. 11/533,839 is a Continuation-In-Part of U.S. patent application Ser. No. 11/261,424 filed on Oct. 28, 2005 now U.S. Pat. No. 8,066,656. The contents of each of the above-identified applications are herein incorporated by reference in their entirety.

FIELD OF THE INVENTION

The present invention relates to an adjustable orthosis for stretching tissue in the human body. In particular, the present invention relates to an adjustable orthosis which can be used for stretching tissue such as ligaments, tendons or muscles around a joint during flexion or extension of the joint.

BACKGROUND OF THE INVENTION

In a joint, the range of motion depends upon the anatomy of that joint and on the particular genetics of each individual. Typically, joints move in two directions, flexion and extension. Flexion is to bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

When a joint is injured either by trauma or by surgery, scar tissue can form, often resulting in flexion or extension contractures. Such conditions can limit the range of motion of the joint, limiting flexion (in the case of an extension contracture) or extension (in the case of a flexion contracture) of the injured joint. It is often possible to correct this condition by use of a range-of-motion (ROM) orthosis.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include U.S. Pat. Nos. 6,599,263, entitled "Shoulder Orthosis;" 6,113,562, entitled "Shoulder Orthosis;" 5,848,979, entitled "Orthosis;" 5,685,830, entitled "Adjustable Orthosis Having One-Piece Connector Section for Flexing;" 5,611,764, entitled "Method of Increasing Range of Motion;" 5,503,619, entitled "Orthosis for Bending Wrists;" 5,456,268, entitled "Adjustable Orthosis;" 5,453,075, entitled "Orthosis with Distraction through Range of Motion;" 5,395,303, entitled "Orthosis with Distraction through Range of Motion;" 5,365,947, entitled "Adjustable Orthosis;" 5,285,773, entitled "Orthosis with Distraction through Range of Motion;" 5,213,095, entitled "Orthosis with Joint Distraction;" and 5,167,612, entitled "Adjustable Orthosis," all to Bonutti and herein are expressly incorporated by reference in their entirety.

SUMMARY OF THE INVENTION

The present invention provides an orthosis for stretching tissue around a joint of a patient between first and second relatively pivotable body portions. The joint and the first and second body portions defining on one side of the joint an inner sector which decreases in angle as the joint is flexed and defining on the opposite side of the joint an outer sector which decreases in angle as the joint is extended.

The orthosis includes a first arm member affixable to the first body portion. The first arm member has a first extension member extending at an angle α therefrom. A second arm member affixable to the second body portion is also included. The second arm member has a second extension member having an arcuate shape extending therefrom. The second and first extension members are operatively connected, such that the second extension member travels through the first extension member along an arcuate path when the second arm member is moved from a first position to a second position relative to the first arm member.

The orthosis further includes a drive assembly for selectively moving the second extension member relative to the first extension member. The drive assembly is mounted onto the first extension member, engaging the second extension member. The drive assembly can be manually or automatically actuated to selectively move the second extension member relative to the first extension member.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention relates to an orthosis for moving a joint between first and second relatively pivotable body portions. The joint and the first and second body portions define on one side (the flexor side) of the joint an inner sector which decreases in angle as the joint is flexed (bent) and on the opposite side (the extensor side) of the joint an outer sector which decreases in angle as the joint is extended (straightened). The orthosis of the present invention is affixable to either the flexor or extensor side of the joint for treatment of flexion or extension contractures.

Figure 1:
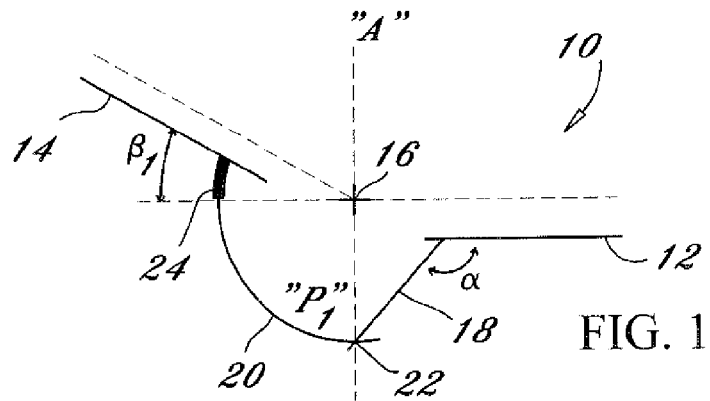
FIG. 1 is a schematic diagram of the orthosis of the present invention in a flexed position.

Referring now to the drawing figures in which like reference designators refer to like elements, there is shown in FIG. 1, a schematic of the orthosis 10 of the present invention. The orthosis 10 includes a first arm member 12 attachable to the first body portion and a second arm member 14 attachable to the second body portion, wherein a joint axis of rotation 16 is interposed between and offset from the first and second arm members 12 and 14. The first and second arm members 12 and 14 are operatively connected to each other offset from the joint axis 16.

The first arm member 12 of the orthosis 10 includes a first extension member 18, which extends at angle α from the first arm member 12. The second arm member 14 of the orthosis 10 includes a second extension member 20 extending therefrom and having an arcuate shape. The first and second extension members 18 and 20 are operatively connected at point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle α between the first extension member 18 and the first arm member 12 and the radius of curvature of the second extension member 20 are a function of the joint to be treated and the degree of flexion or extension contractures.

The orthosis further includes a drive assembly 22 at point "P." The drive assembly connects the first and second extension members 18 and 20 for applying force to the first and second arm members 12 and 14 to pivot the first and second body portions relative to each other about the joint.

Figure 2:
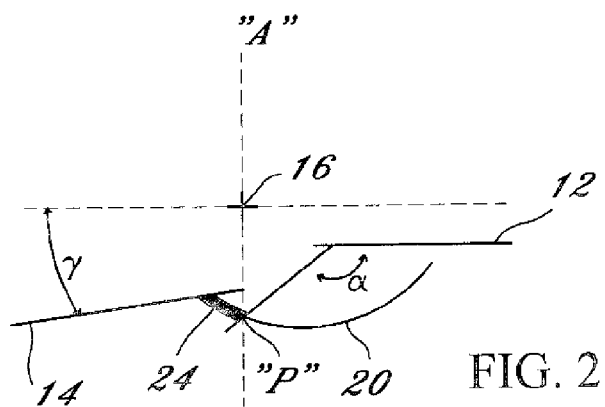
FIG. 2 is a schematic diagram of the orthosis of the present invention in an extended position.

The orthosis 10 of the present invention is shown having an angle α such that the operative connection, at point "P," of the first and second extensions 18 and 20 is located in a plane "A" passing through the joint axis 16, wherein plane "A" is substantially orthogonal to a longitudinal axis of the first arm member 12. This position of point "P" provides an angle $\beta_1$ between the second arm member 14 and the joint axis 16, wherein $\beta_1$ is the maximum angle of flexion. As shown in FIG. 2, the second extension member includes a stop 24. The stop 24 acts to limit the angle of maximum extension γ between the second arm member 14 and the joint axis 16. An increase in the length of the stop 24 will decrease the angle of maximum extension γ. A decrease in the length of the stop 24 will increase the angle of maximum extension γ.

Figure 3:
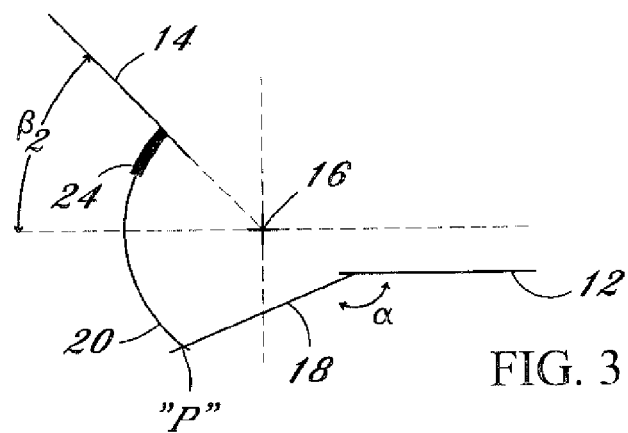
FIG. 3 is a second schematic diagram of the orthosis of the present invention in a flexed position.

Referring to FIG. 3, the maximum flexion angle can be increased by increasing the angle α. An increase in the angle α will move the point "P" to a location "in front of" the plane "A." This position of point "P" provides an angle $\beta_2$ between the second arm member 14 and the joint axis 16 in maximum flexion, wherein $\beta_2$ is greater than $\beta_1$ The greater the angle $\alpha_1$, the greater the angle of maximum flexion.

Alternatively, (not shown) a decrease in the angle α will move the point "P" to a location "behind" the plane "A." This position of point "P" provides an angle $\beta_3$ between the second arm member 14 and the joint axis 16 in maximum flexion, wherein $\beta_3$ is less than $\beta_1$ The smaller the angle α, the smaller the angle $\beta_3$ of maximum flexion.

Figure 4:
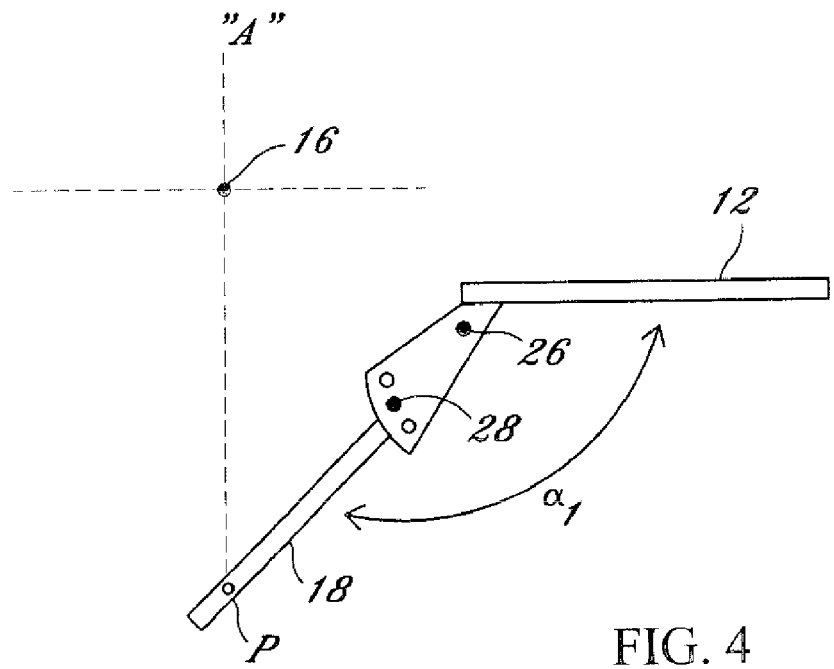
FIG. 4 shows an adjustable first extension member of the orthosis of the present invention.

Referring to FIG. 4, the first extension member 18 is selectively, pivotally connected at location 26 to the first arm member 12. The pivotal connection 26 of the first extension member 18 permits the angle α between the first extension member 18 and the first arm member 12 to be selectively increased and decreased, increasing and decreasing the range of motion. In a first position 28, the first extension member 18 is positioned at an angle $\alpha_1$, wherein the operative connection, at point "P," of the first and second extension members 18 and 20 is located in a plane "A" passing through the joint axis 16, wherein plane "A" is substantially orthogonal to a longitudinal axis of the first arm member 12. The first position 28 of point "P" provides a maximum angle of flexion of $\beta_1$. The second extension member stop 24 acts to limit the angle of maximum extension $\gamma_1$ between the second arm member 14 and the joint axis 16.

Figure 5:
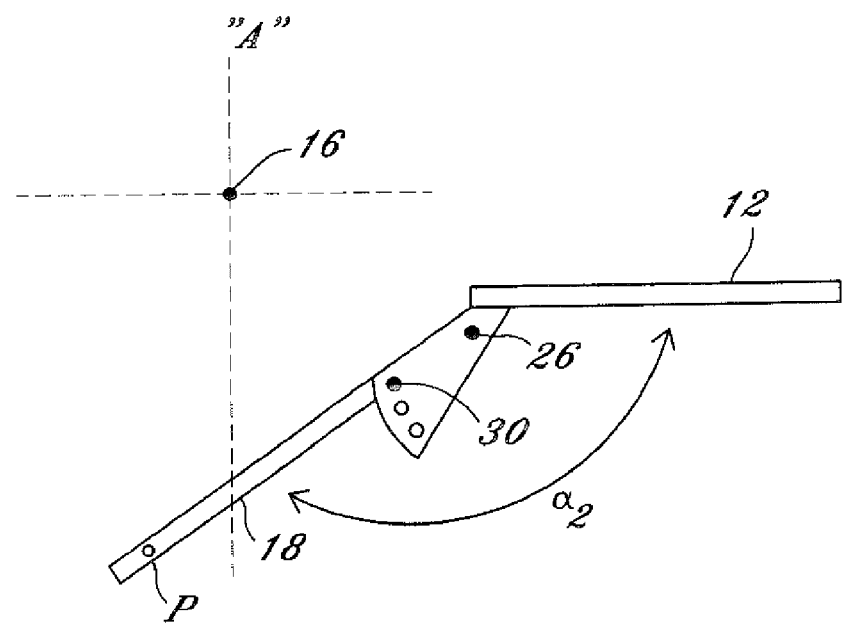
FIG. 5 shows the adjustable first extension member of FIG. 4 in a second position.

Referring to FIG. 5, in a second position 30 the angle $\alpha$ is increased to an angle $\alpha_2$, positioning the point "P" to a location "in front of" the plane "A." The second position 30 of point "P" provides a maximum angle of flexion of $\beta_2$, wherein $\beta_2$ is greater than $\beta_1$. The second extension member stop 24 acts to limit the angle of maximum extension $\gamma_2$ between the second arm member 14 and the joint axis, wherein $\gamma_2$ is less the $\gamma_1$.

The selective pivotal connection 26 of the first extension member 18 to the first arm member 12 can have a plurality of selectable positions. The angle $\alpha$ between the first arm member 12 and the first extension 18 can be selectively increased to move the point "P", on, "in front of" or "behind" the plane "A." It is also envisioned that a positioned can be selected to increase the angle $\alpha$ between the first arm member 12 and the first extension 18 sufficiently to move the point "P" "in front of" plane "A" and "above" the longitudinal axis of the first arm member 12, maximizing the maximum angle of flexion $\beta$.

The orthosis 10 of the present invention can be connected to the flexor side of the first and second body portions of the joint, which results in a decrease in angle as the joint is flexed (bent) and an increase in angle and the joint is extended (straightened). Alternatively, orthosis 10 of the present invention can be connected to the extensor side of the joint, which results in a decrease in angle as the joint is extended straightened and an increase in angle as the joint is flexed (bent).

Figure 6:
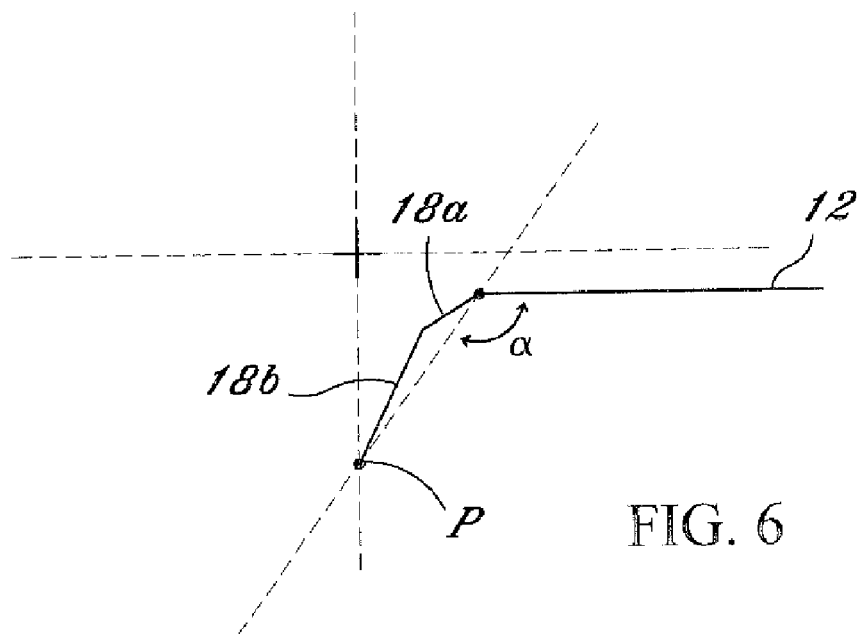
FIG. 6 shows a segmented first extension member of the present invention.
Figure 7:
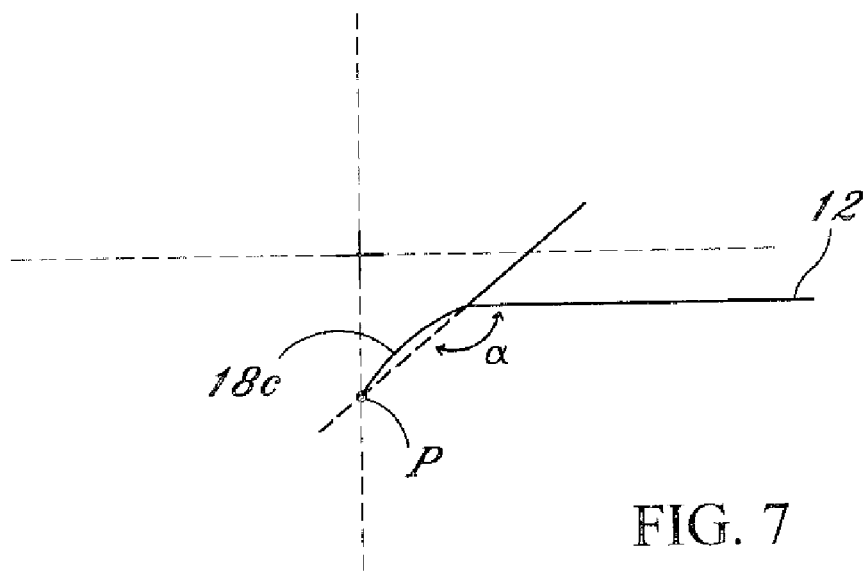
FIG. 7 shows an arcuate first extension member of the present invention.

The previous description of the first arm member 12 depicts a first extension 18 having a substantially linear shape, extending at an angle $\alpha$ from the first arm member 12. However, it is within the scope of the present invention that the first extension member 18 can be any shape extending from the first arm member 12 which positions the point "P" in the desired relationship to the plane "A." Referring to FIG. 6, a segmented first extension member is shown, including a first extension member segment 18a and a second extension member segment 18b. The first and second extension member segments 18a and 18b extend from the first arm member 12, positioning the point "P" at an angle $\alpha$ from the first arm member 12. Referring to FIG. 7, an arcuate first extension member 18c is shown. The arcuate extension member 18c extends from the first arm member 12, positioning the point "P" at an angle $\alpha$ from the first arm member 12.

Figure 8:
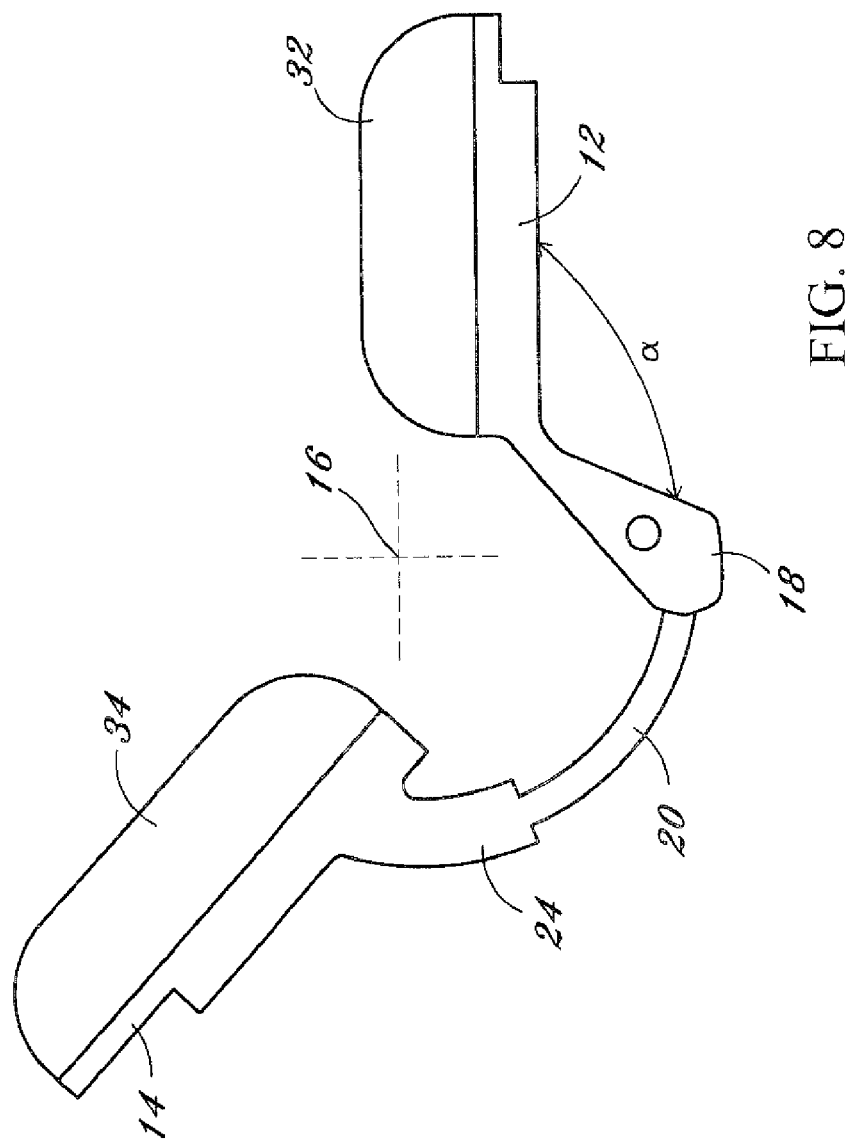
FIG. 8 shows an orthosis of the present invention.

Referring to FIG. 8, the orthosis 10 of the present invention includes a first arm member 12 attachable to the first body portion and a second arm member 14 attachable to the second body portion, wherein the joint axis 16 is interposed between and offset from the first and second arm members 12 and 14. The first and second arm members 12 and 14 are connected with each other offset from the joint axis 16.

The first arm member 12 of the orthosis 10 includes a first extension member 18, which extends at angle $\alpha$ from the first arm member 12. The second arm member 14 of the orthosis 10 includes a second extension member 20, having an arcuate shape. The first and second extension members 18 and 20 are operatively connected a point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle $\alpha$ between the first extension member 18 and the first arm member 12 and the radius of curvature of the second extension member 20 are a function of the joint to be treated and the degree of flexion or extension contractures.

A first cuff 32 is attached to the first arm member 12, wherein the first cuff 32 is positionable about the first body portion. The first cuff 32 is attached to the first body portion by cuff straps. The first cuff 32 secures the first body portion to the first arm member 12. A second cuff 34 is attached to the second arm member 14, wherein the second cuff 34 is positionable about the second body portion. The second cuff 34 is attached to the second body portion by cuff straps. The second cuff 34 secures the second body portion to the second arm member 14. (The term "cuff" as used herein means any suitable structure for transmitting the force of the orthosis 10 to the limb portion it engages.)

In an exemplary use, the orthosis 10 is operated to extend a joint in the following manner. The first cuff 32 is fastened about the first body portion tightly enough that the first arm member 12 may apply torque to the first body portion without having the first cuff 32 slide along the first body portion. Similarly, the second cuff 34 is fastened securely around the second body portion so that the second arm member 14 may apply torque to the second body portion without the second cuff 34 sliding along the second body portion. The orthosis 10 is attached to the first and second body portions in a first position. The second arm member 14 is rotated from the first position to a second position, relative to the first arm member 12, rotating the second body portion about the joint axis 16 stretching the joint. As the second arm member 14 is rotated to the second position, the second extension member 20 travels along an arcuate path about and substantially through point "P." The orthosis 10 is maintained in the second position for a predetermined treatment time providing a constant stretch to the joint. After the expiration of the treatment time, the second arm member 14 is moved back to the first position, relieving the joint. Optionally, the second arm member 14 can be rotated to a third position, increasing the stretch on the joint. The second arm member 14 can be rotated at discrete time intervals to incrementally increase the stretch of the joint through the treatment cycle. After completion of the treatment cycle, the second arm member is returned to the first position for removal of the orthosis 10.

The first and second arm members 12 and 14 are rigid members made of, for example, aluminum, stainless steel, polymeric, or composite materials. The arms are rigid so as to be able to transmit the necessary forces. It should be understood that any material of sufficient rigidity can be used.

In an embodiment, the components of the orthosis 10 of the present invention are made by injection molding. Generally for injection molding, tool and die metal molds of the orthosis 10 components are prepared. Hot, melted plastic material is injected into the molds. The plastic is allowed to cool, forming components. The components are removed from the molds and assembled. The cuff portions 32 or 34 can be individual molded and attached to the arm members 12 or 14. Alternatively, the cuff portions can be molded as an integrated part of the arm members 12 or 14.

In use, the orthosis 10 can be connected to the flexor side of the first and second body portions of the joint, which results in a decrease in angle as the joint is flexed (bent) and an increase in angle as the joint is extended (straightened). Alternatively, orthosis 10 of the present invention can be connected to the extensor side of the joint, which results in a decrease in angle as the joint is extended straightened and an increase in angle as the joint is flexed (bent).

In an embodiment, the orthosis 10 includes a first cuff 32 for attachment to a first body portion, and a second cuff 34 for attachment to a second body portion. The first body portion is joined to the second body portion at a joint, around which is located, as is well known, soft tissue. Each of the first and second cuffs 32 and 34 includes loop connectors for receiving straps extending around the body portions to clamp the cuffs 32 and 34 to the body portions.

The first cuff 32 is mounted for sliding movement on the first arm member 12 and is slidable along the first arm member 12 in a manner as described below. The second cuff 34 is mounted for sliding movement on a second arm member 14 and is slidable along the second arm member 12 in a manner as described below.

Bending a Joint in Extension:

In operation of the orthosis 10 to extend the joint, the orthosis 10 starts at a more flexed position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the joint.

As the orthosis 10 is rotated from the first position to the second position, extending the joint, the first and second cuffs 32 and 34 move along the first and second arm members 12 and 14. The first cuff 32 moves inwardly along the first arm member 12. Similarly, the second cuff 34 moves inwardly along the second arm member 14. Because the cuffs 32 and 34 are clamped onto the first and second body portions as described above, the outward pivoting movement of the first and second arm members 12 and 14 and the cuffs 32 and 34 causes the joint to be extended as desired. However, this extension of the joint can place strong distractive forces on the soft tissues around the joint. The sliding movement of the cuffs 32 and 34, inwardly along the first and second arm members 12 and 14, helps to limit these distractive forces by counteracting the outward movement of the first and second arm members 12 and 14. The cuffs 32 and 34 slide inwardly along the first and second arm members 12 and 14 a distance far enough so that the joint is only slightly distracted during extension. Thus, the detrimental effects of strong distractive forces normally generated in forced extension of a joint are avoided, being replaced with the beneficial effects of limited and controlled distraction.

Bending a Joint Flexion:

In operation of the orthosis 10 to flex the joint, the orthosis 10 starts at a more extended position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels about and substantially though point "P," along an arcuate path. The orthosis 10 is maintained in the second position for a predetermined treatment time providing a constant stretch to the joint.

As the orthosis 10 is rotated from the first position to the second position, flexing the joint, the first and second cuffs 32 and 34 move along the first and second arm members 12 and 14. The first cuff 32 moves outwardly along the first arm member 12. Similarly, the second cuff 34 moves outwardly along the second arm member 14. Because the cuffs 32 and 34 are clamped onto the first and second body portions the inward pivoting movement of the first and second arm members 12 and 14 and the cuffs 32 and 34 causes the joint to be flexed as desired. However, this flexion of the joint can place strong compressive forces on the soft tissues around the joint. The sliding movement of the cuffs 32 and 34, outwardly along the first and second arm members 12 and 14, helps to limit these compressive forces by counteracting the inward movement of the first and second arm members 12 and 14. The cuffs 32 and 34 slide outwardly along the first and second arm members 12 and 14 a distance far enough so that the joint is only slightly compressed during flexion. Thus, the detrimental effects of strong compressive forces normally generated in forced flexion of a joint are avoided, being replaced with the beneficial effects of limited and controlled compression.

Figure 9:
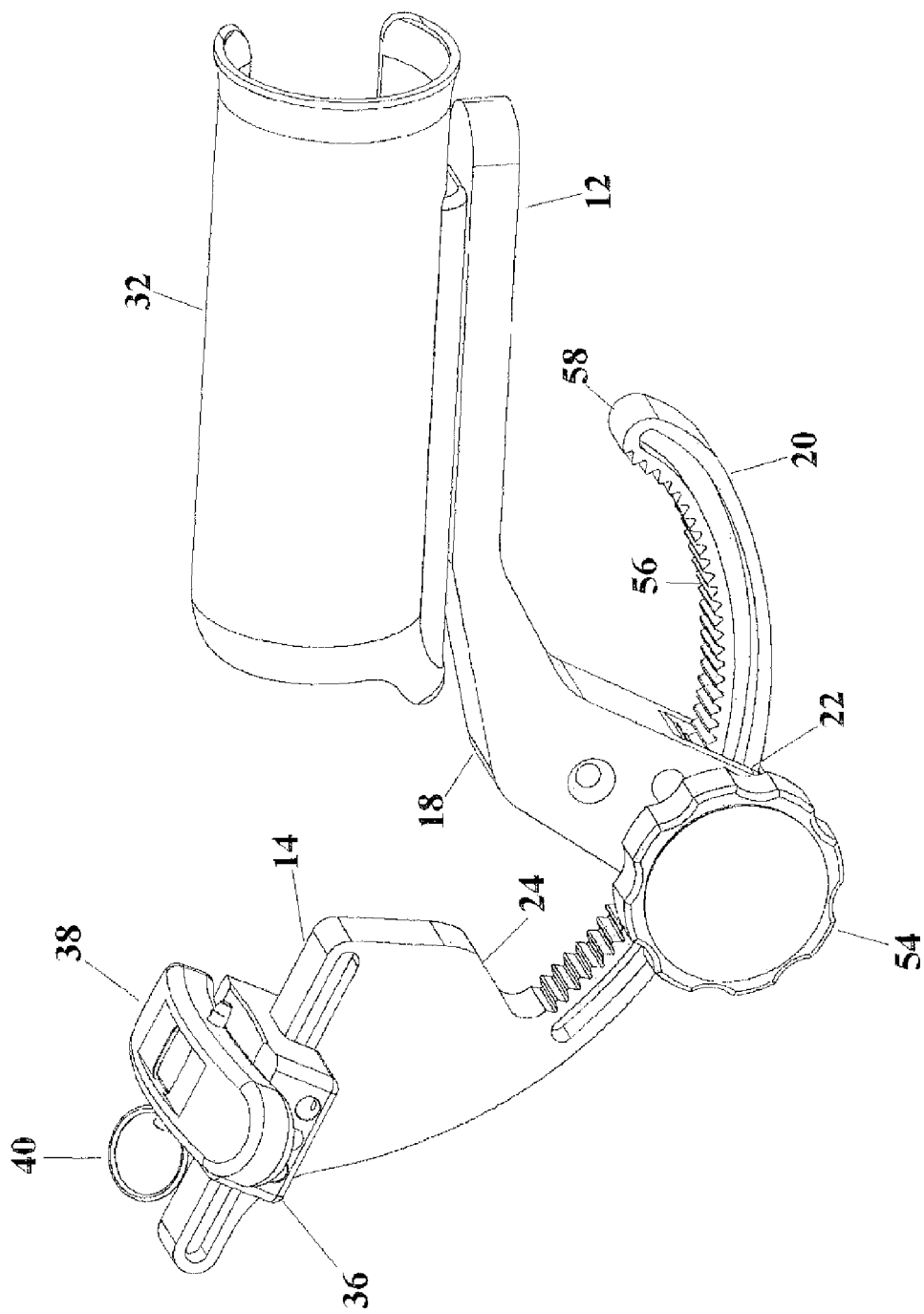
FIG. 9 shows an orthosis of the present invention for flexing and extending a wrist joint in a patient.

Referring now to FIG. 9, the orthosis 10 can be used to bend a wrist in flexion or extension. The orthosis 10 includes a first arm member 12 attachable to the forearm of a patient. The first cuff 32 is clamped onto the forearm by straps. A second arm member 14, operatively connected to the first arm member 12, is attachable to the hand of the patient, wherein the axis of the wrist joint is interposed between and offset from the first and second arm members 12 and 14. The second arm member 14 includes a base member 36 attach thereto. A hand pad 38 is attached to the base member 36. The hand pad 38 is clamped onto the hand by straps, tightly enough so that the second arm member 14 can apply torque to the joint. The hand pad 38 can be shaped to conform to the palm or the back surface of the hand.

Bending Wrist in Flexion:

When a wrist is to be bent in flexion, the first cuff 32 is connected with the forearm and the hand pad 38 is connected with the palm of the hand. The first cuff 32 and hand pad 38 are clamped onto the forearm and hand, respectively, by straps, tightly enough so that they can apply torque to flex the joint. The second arm member 14 is rotated from the first position to a second position, relative to the first arm member 12, rotating the hand about the wrist joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the wrist joint.

Bending Wrist in Extension:

When a wrist is to be bent in extension, the first cuff 32 is connected with the forearm and the hand pad 38 is connected with the back surface of the hand. The first cuff 32 and hand pad 38 are clamped onto the forearm and back surface of the hand, respectively, by straps, tightly enough so that they can apply torque to flex the joint. The second arm member 14 is rotated from the first position to a second position, relative to the first arm member 12, rotating the hand about the wrist joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the wrist joint.

In an embodiment, the hand pad 38 is removable attached to the base member 36. The hand pad 38 includes a first surface, which has a substantially convex shape, to conform to the palm of the hand. A second surface, opposite the first surface, is also included, having a substantially concave shape, to conform to the back surface of the hand. The hand pad 38 can be removable attached to the base member 36 such that the first or second surfaces engages the hand of the patient.

For example, the hand pad 38 is removably secured to base member 36 by detent pin 40. The removable securing of the hand pad 38 allows the orthosis 10 to be used for both flexion and extension of the wrist. In flexion, the hand pad 38 is connected to the base member 36 with the first surface facing "up" to conform to the palm of the hand. In extension, the hand pad 38 is connected to the base member 36 with the second surface facing "up" to conform to the back surface of the hand.

The base member 38 can be mounted for sliding movement on the second arm member 14 and is slidable along the second arm member 14 in a manner as described below.

Bending Wrist in Extension:

In operation of the orthosis 10 to extend the wrist joint, the orthosis 10 starts at a more flexed position. The first cuff 32 is connected with the forearm and the hand pad 38 is connected with the palm of the hand. The first cuff 32 and hand pad 38 are clamped onto the forearm and palm of the hand so as to apply torque to extend the wrist joint. The second arm member 14 is rotated from the first position to a second position, relative to the first arm member 12, rotating the hand about the wrist joint axis 16 stretching the wrist joint. As the second arm member 14 is rotated to the second position the second extension member 20 travels along an arcuate path about and substantially through point "P." The orthosis 10 is maintained in the second position for a predetermined treatment time providing a constant stretch to the joint.

As the orthosis 10 is rotated from the first position to the second position, extending the joint, the base member 36 and hand pad 38 move along the second arm member 14. The base member 36 and hand pad 38 move inwardly along the second arm member 14. Because the cuff 32 and hand pad 38 are clamped onto the forearm and hand the outward pivoting movement of the first and second arm members 12 and 14 causes the joint to be extended as desired. However, this extension of the joint can place strong distractive forces on the soft tissues around the joint. The sliding movement of the base member 36 and hand pad 38, inwardly along the second arm member 14, helps to limit these distractive forces by counteracting the outward movement of the second arm members 12 and 14. The base member 36 and hand pad 38 slide inwardly along the second arm member 14 a distance far enough so that the joint is only slightly distracted during extension. Thus, the detrimental effects of strong distractive forces normally generated in forced extension of a joint are avoided, being replaced with the beneficial effects of limited and controlled distraction.

Bending Wrist in Flexion:

In operation of the orthosis 10 to flex the wrist joint, the orthosis 10 starts at a more extended position. The first cuff 32 is connected with the forearm and the hand pad 38 is connected with the back surface of the hand. The first cuff 32 and hand pad 38 are clamped onto the forearm and back surface of the hand so as to apply torque to flex the wrist joint. The second arm member 14 is rotated from the first position to a second position, relative to the first arm member 12, rotating the hand about the wrist joint axis 16 stretching the wrist joint. As the second arm member 14 is rotated to the second position the second extension member 20 travels along an arcuate path about and substantially through point "P." The orthosis 10 is maintained in the second position for a predefined treatment time providing a constant stretch to the joint.

As the orthosis 10 is rotated from the first position to the second position, flexing the joint, the base member 36 and hand pad 38 move along the second arm member 14. The base member 36 and hand pad 38 move outwardly along the second arm member 14. Because the cuff 32 and hand pad 38 are clamped onto the forearm and hand the inward pivoting movement of the first and second arm members 12 and 14 causes the joint to be flexed as desired. However, this flexing of the joint can place strong compressive forces on the soft tissues around the joint. The sliding movement of the base member 36 and hand pad 38, outwardly along the second arm member 14, helps to limit these compressive forces by counteracting the inward movement of the first and second arm members 12 and 14. The base member 36 and hand pad 38 slide outwardly along the second arm member 14 a distance far enough so that the joint is only slightly compressed during extension. Thus, the detrimental effects of strong compressive forces normally generated in forced flexion of a joint are avoided, being replaced with the beneficial effects of limited and controlled compression.

In the above description, the hand pad 38 is shown sliding inwardly and outwardly along the second arm member 14. However, it is contemplated that the hand pad 38 can slide in other directions. For example, the hand pad 38 can slide substantially orthogonal to the second arm member 14, wherein the substantially orthogonal directions can have an arcuate path. Similarly, as discussed in more detail below, it is contemplated within the scope of the present invention that hand pad 38 can be connected to the second arm member 14 such that hand pad 38 can exhibit both longitudinal and orthogonal motion (and combinations thereof) with respect to the second arm member 14.

In the above description, the second extension member 20 is shown and described as having a substantially circular arcuate shape, positioning the axis of rotation at the joint axis 16. However, it is contemplated that the second extension member 20 can have alternative shapes.

Figure 10:
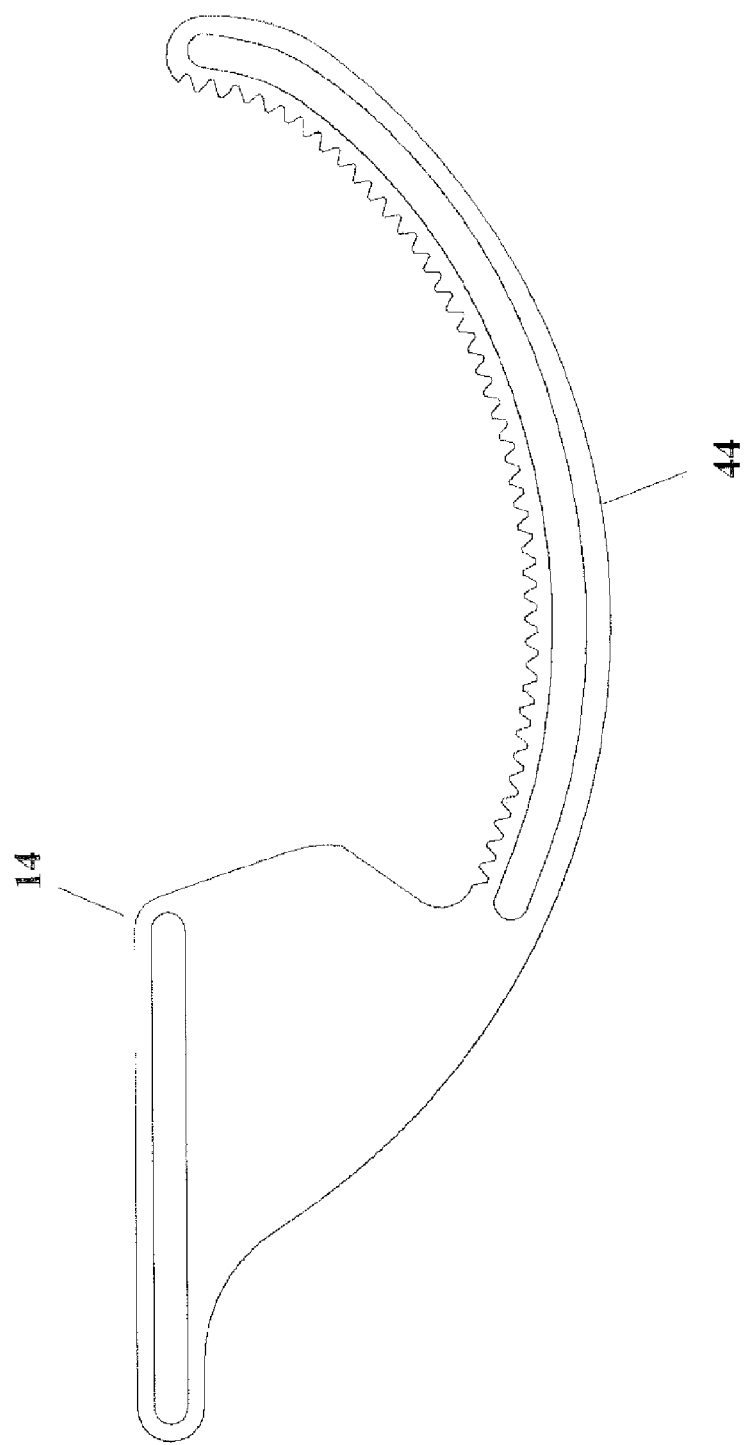
FIG. 10 shows a non-circular arcuate shaped second extension member of the present invention.

Referring to FIG. 10, the second arm member 14 is shown having a non-circular arcuate shaped second extension member 44. The non-circular arcuate shaped second extension member 44 provide an axis of rotation which changes as the second arm member 14 is moved from the first position to the second portion. As such, as the second arm member 14 is moved from the first position to the second portion the second body portion will exhibit both a rotational motion, about the joint axis 16, and a translational motion, distracting or compressing the joint.

Figure 11:
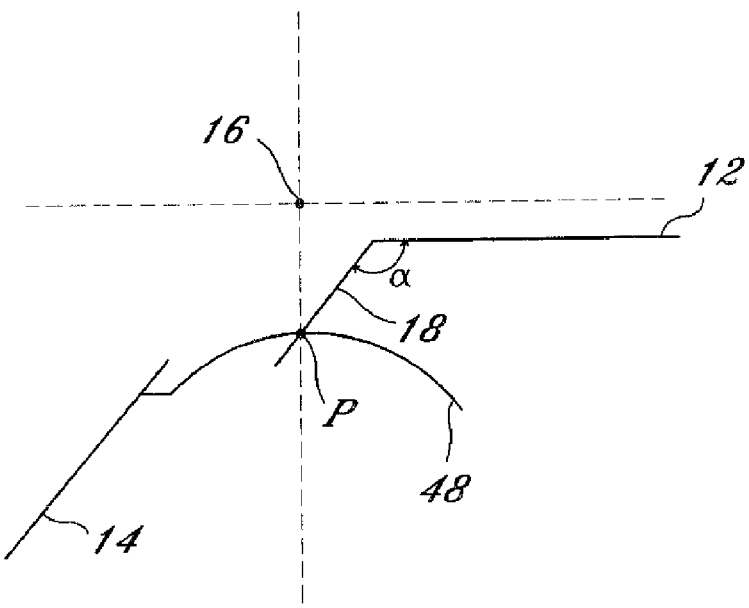
FIG. 11 shows an alternative arcuate shaped second extension member of the present invention.

In the previously described embodiments, the arcuate shape of the second extension member 20 or 44 as shown have concave radius of curvature relative to the joint 16. However, referring to FIG. 11, it is contemplated that the second extension member 18 or 44 can have a convex radius of curvature relative to the joint 16. Similar to the concave radius of curvature, the convex arcuate shape of the second extension member 18 or 44 results in the second body portion rotating about the joint axis 16, when the second arm member 14 is moved from a first position to a second position relative to the first arm member 12.

Figure 12:
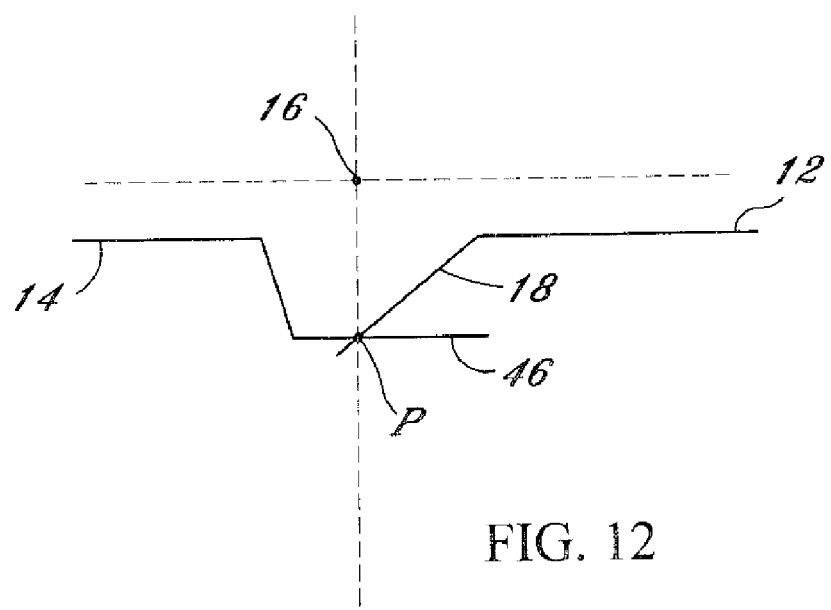
FIG. 12 shows a linear shaped second extension member of the present invention.

Referring to FIG. 12, the second arm member 14 of the orthosis 10 includes a second extension member 48 extending therefrom and having a linear shape. The first and second extension members 18 and 48 are operatively connected at point "P," such that in operation the second extension member 48 travels along a linear path through point "P." The linear shape of the second extension member 48 results in the second body portion being translated with respect to the first body portion. The translational movement of the second arm member 14 results is a distraction or compression of the joint when the second arm member 14 is moved from a first position to a second position relative to the first arm member 12.

As discussed further below, the hand pad can be mounted for translational and rotational movement on the base member.

Figure 13A:
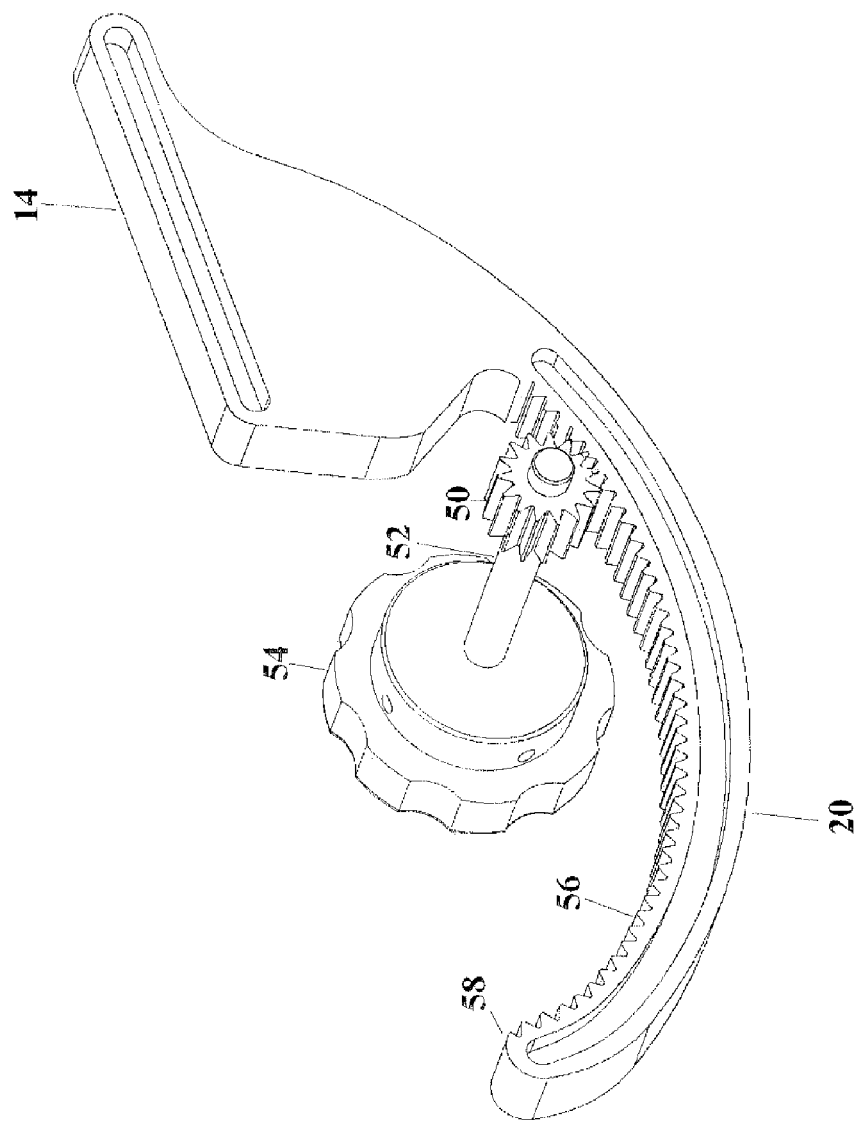
FIGS. 13A and B show exemplary drive assemblies of the present invention.

Drive Assembly:

Referring to FIGS. 9 and 13A, the drive assembly 22 of the orthosis includes a gear system. As previously noted, the components of the orthosis, including the drive assembly 22, can be made by injection molding a polymer. The drive assembly 22 is supported in the first extension member 18, including a gear 50 rotatable about point "P." A shaft 52, attached to the gear 50, extends from first extension member 18. A knob 54 is connected to the shaft 52, opposite the gear 50, for manually rotating the gear 50. The second extension member 20 includes a series of teeth 56 along an inner surface 58. The second extension member 20 is threaded through the first extension member 18, such that the teeth 56 on the second extension member 20 engage the gear 50. The rotation of the knob 56 causes the gear 50 to rotate, pushing or pulling the second extension member 20 through the first extension member 18. The drive assembly 22 includes a locking or breaking mechanism which prevents the gear 50 from rotating absent am applied force rotation of the knob 46. Such a lock or breaking mechanism can include a compression washer or other known gear locking or breaking mechanisms.

Figure 13B:
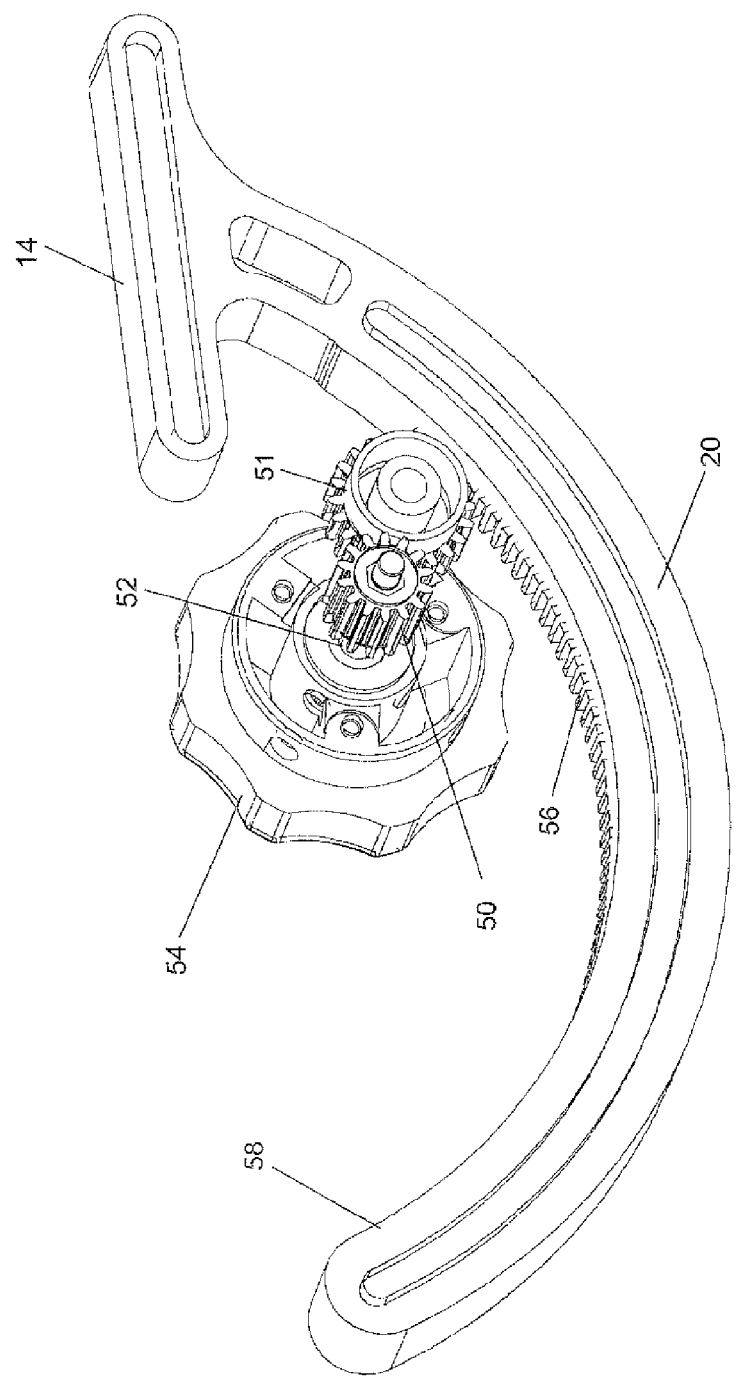

In another embodiment, as shown in FIG. 13B, the shaft 52 is attached to the gear 50 and extends from first extension member 18. The knob 54 is connected to the shaft 52 opposite the gear 50 for manually rotating the gear 50. The second extension member 20 includes a series of teeth 56 along an inner surface 58. The teeth 56 can extend fully or partially along the width of the inner surface 58. A secondary gear 51 is positioned between the gear 50 and the inner surface 58, where the secondary gear 51 engages gear 50. The second extension member 20 is threaded through the first extension member 18, such that the teeth 56 on the second extension member 20 engage the secondary gear 51. The rotation of the knob 56 causes the gear 50 to rotate, thereby rotating the secondary gear 51 and pushing or pulling the second extension member 20 through the first extension member 18. The ratio between gear 50 and secondary gear 51 is selected to permit an easy rotation of the knob 54, moving of the second extension member 20 through the first extension member 18. The drive assembly 22 includes a locking or breaking mechanism which prevents the gear 50 from rotating absent am applied force rotation of the knob 46. Such a lock or breaking mechanism can include a compression washer or other known gear locking or breaking mechanisms.

The drive assembly 22 is described as utilizing a gear system. However, it is contemplated that other known drive systems can be used to move the second extension member 20 through the first extension member 18, for example a friction type drive system. Regardless of the drive system used, the joint orthosis of the present invention can act as a brace, restricting the relative movement of the first and second body portions to one degree of freedom (e.g. flexion and extension about the joint). Thus, drive assembly 22 can be configured to allow free motion in one degree of freedom. This can be achieved in a number of different ways. For example, gear 50 can be positioned such that it does not engage teeth 56.

In an alternative embodiment, the drive assembly 22 for an orthosis 10 in accordance with the present invention can be actuated by a motor instead of by a manually actuatable member, such as the knob 54.

In an embodiment, an electric motor is mounted to the shaft 52 for rotation of the gear 50. A battery provides electric power to the motor. Alternatively, the motor can be supplied with external power. A microprocessor controls the operation of the motor. The microprocessor and motor together can be used to cycle the first and second arm members 12 and 14 through extension and flexion; to move the first and second arm members 12 and 14 in one pivotal direction a certain amount, hold there while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. The programming and control of the microprocessor is within the skill of the art as it relates to driving the motor to control the first and second arm members 12 and 14 to move in known manners. This embodiment is ideally suited for continuous passive motion exercise, because the orthosis is portable and because the motor can be programmed with the desired sequence of movements.

It should be understood that the particular physical arrangement of the motor, the battery, and the microprocessor is not the only possible arrangement of those elements. The invention contemplates that other arrangements of these or similarly functional elements are quite suitable, and thus, the invention is intended to cover any such arrangement. Additionally, another type of power source, other than an electric motor, can also be used. For example, the use of a hydraulic or pneumatic motor as the drive mechanism is contemplated.

Figure 14:
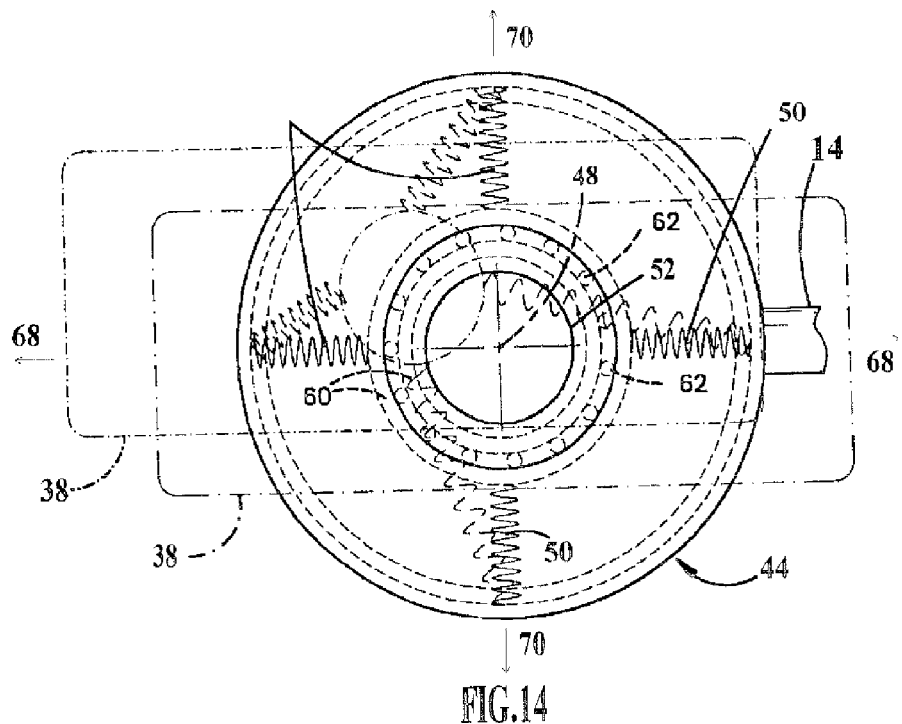
FIG. 14 is a top plan view of portions of an articulating hand pad support of the present invention.
Figure 15:
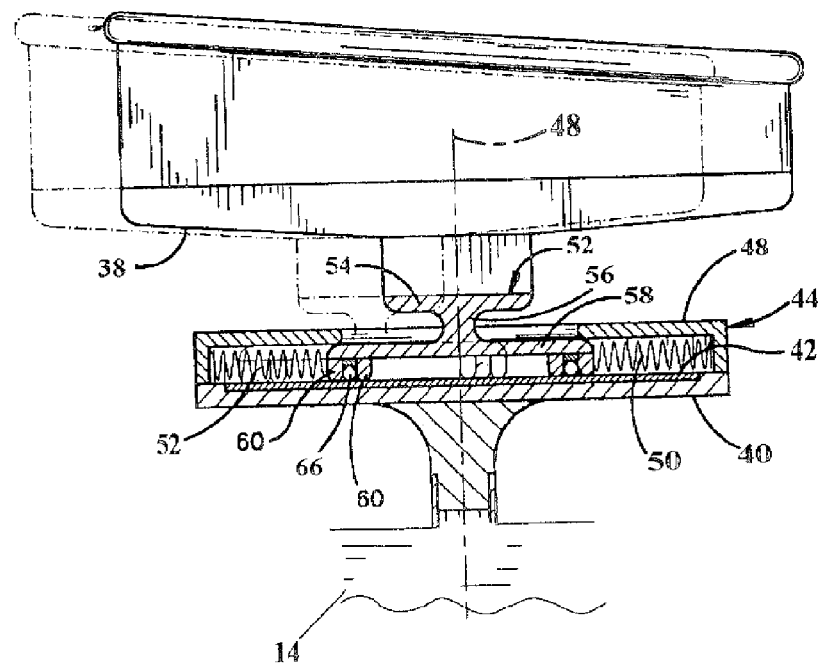
FIG. 15 is a schematic sectional view of the articulating hand pad support of FIG. 14.

Referring to FIGS. 14 and 15, another embodiment in which the hand pad 38 articulates with respect to the second arm member 14 is shown. The second arm member 14 has a circular base member 40 attached thereto. The circular base member 40 supports a circular base plate 42. A circular cover 44 extends upwardly from the circular base member 40 and has a portion 46 extending radially inwardly toward a vertical axis 48 to define a slide chamber 50.

A hand pad support slider 52 is received in the slide chamber 50. The support slider 52 has an upper portion 54 to which the hand pad 38 is attached. The upper portion 54 is connected by a neck 56 to a circular planar portion 58. Two annular bearing races 60 extend downwardly from the planar portion 58 and secure between them a plurality of ball bearings 62. A washer 64 is disposed above the bearings 62. The ball bearings 62 support the slider 52 and thus the hand pad 38 for sliding movement in any direction within the slide chamber 50. The hand pad 38 can be made self-centering by springs 66.

Thus, the hand pad 38 is slidable relative to the circular base member 40 in any direction for a limited extent. As indicated by the arrow 68, the hand pad 38 is slidable fore and aft within the extent of travel allowed by the support slider 52 within the slide chamber 50. As indicated by the arrow 70, the hand pad 38 is slidable laterally within the extent of travel allowed by the support slider 52 within the slide chamber 50. With these two combined, it can be seen that the roller bearing assembly provides a compound of movement of the hand pad 38.

Figure 16:
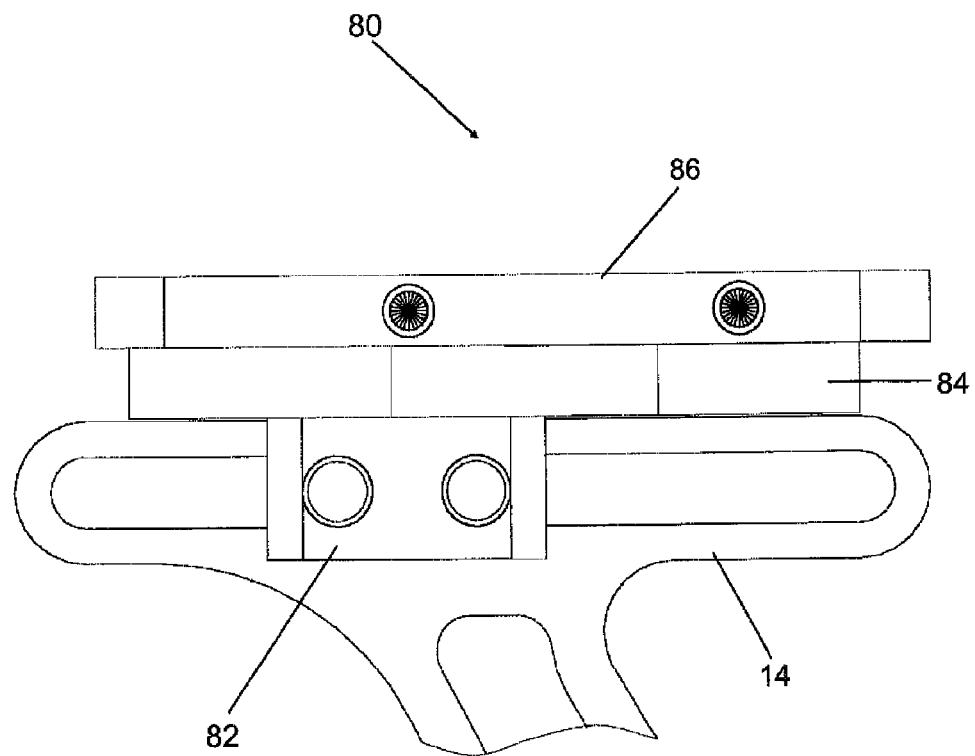
FIG. 16 depicts a side view of another articulating hand pad support of the present invention.
Figure 17A:
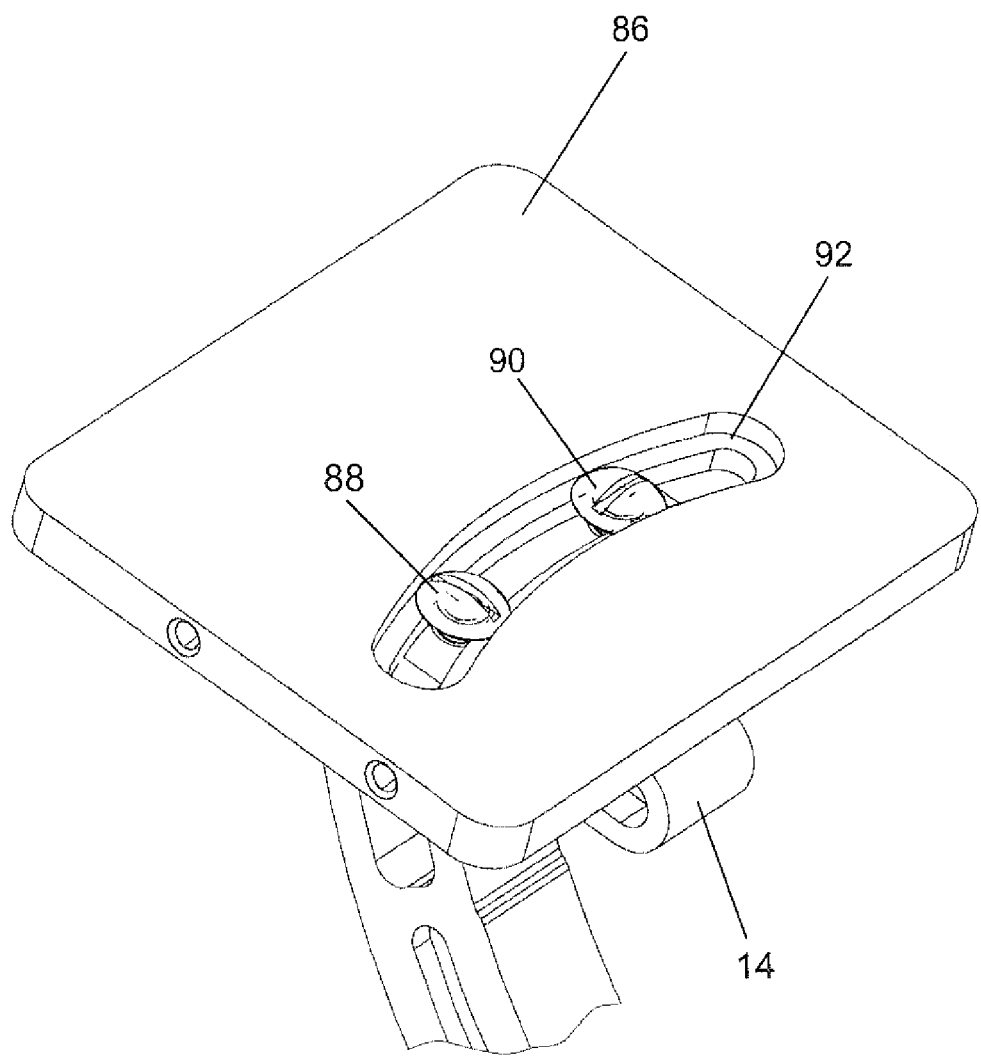
FIG. 17A depicts a top view of the articulating hand pad support of FIG. 16.
Figure 17B:
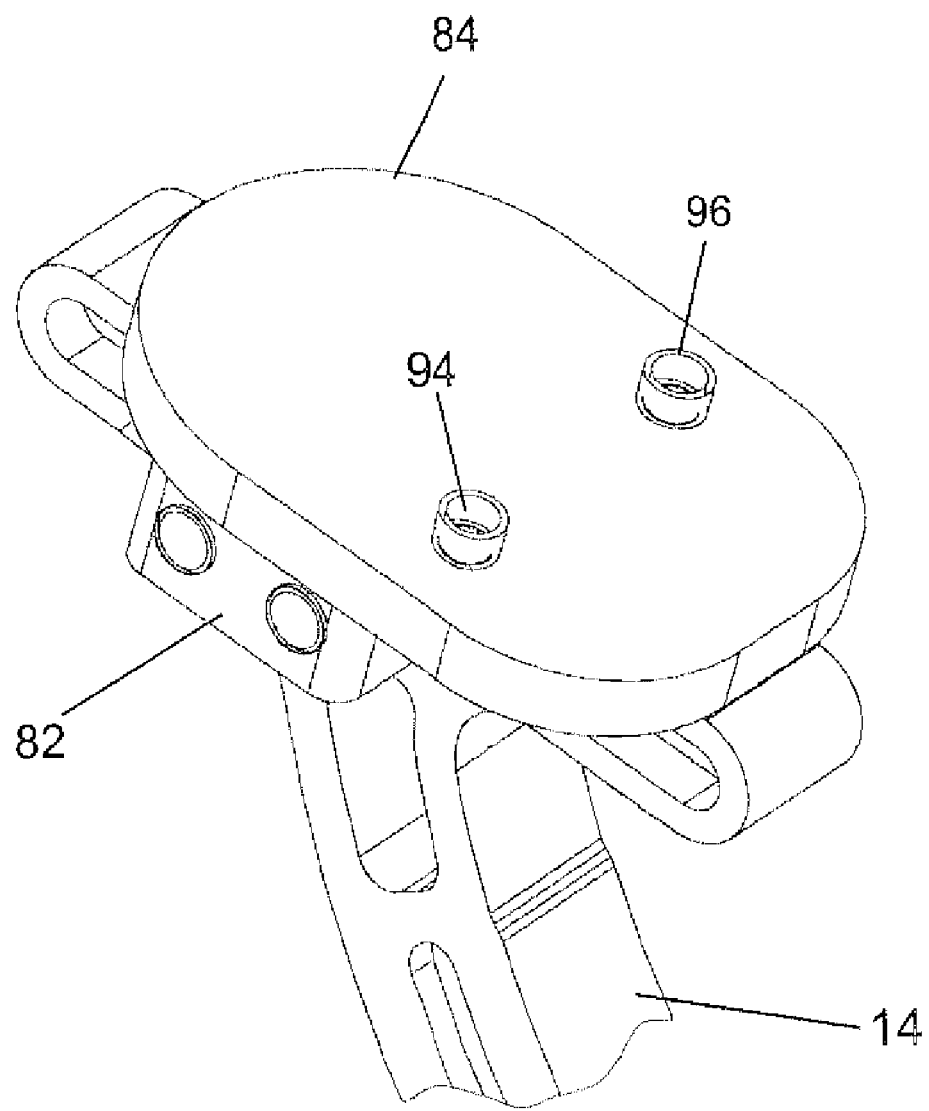
FIG. 17B depicts a top view of the articulating hand pad support of FIG. 16 with the pivoting plate removed.

Referring to FIGS. 16, 17A and 17B, another embodiment 80 in which the hand pad 38 articulates with respect to the second arm member 14 is shown. The second arm member 14 has a sliding base member 82 slidingly mounted thereto in similar fashion to base member 36. The sliding base member 82 supports a fixed base plate 84 attached thereto. A pivotal base plate 86 is pivotally connected to the fixed base plate 84, where the pivotal base 86 plate can arcuately pivot with respect to the fixed base plate 84 and the second arm member 14.

The pivotal base plate 86 is pivotally secured to the fixed base plate 84 by threaded members 88 and 90 extending through an arcuate slot 92 in the pivotal base plate 86. The threaded members 88 and 90 are threaded in threaded holes 94 and 96 in the fixed plate 84. In this manner the pivotal base plate 86 can travel along the arcuate slot 92 with respect to the fixed base plate 84. The hand pad (not shown) can be removable attached to the pivotal base plate 86.

In instances where a joint is misaligned, fixing the position of the joint can result in unwanted torsional forces being applied to the joint. The articulation of the hand pad permits the joint to self align, such that the joint can be rotated about its axis without the application of torsional forces on the joint.

Figure 18:
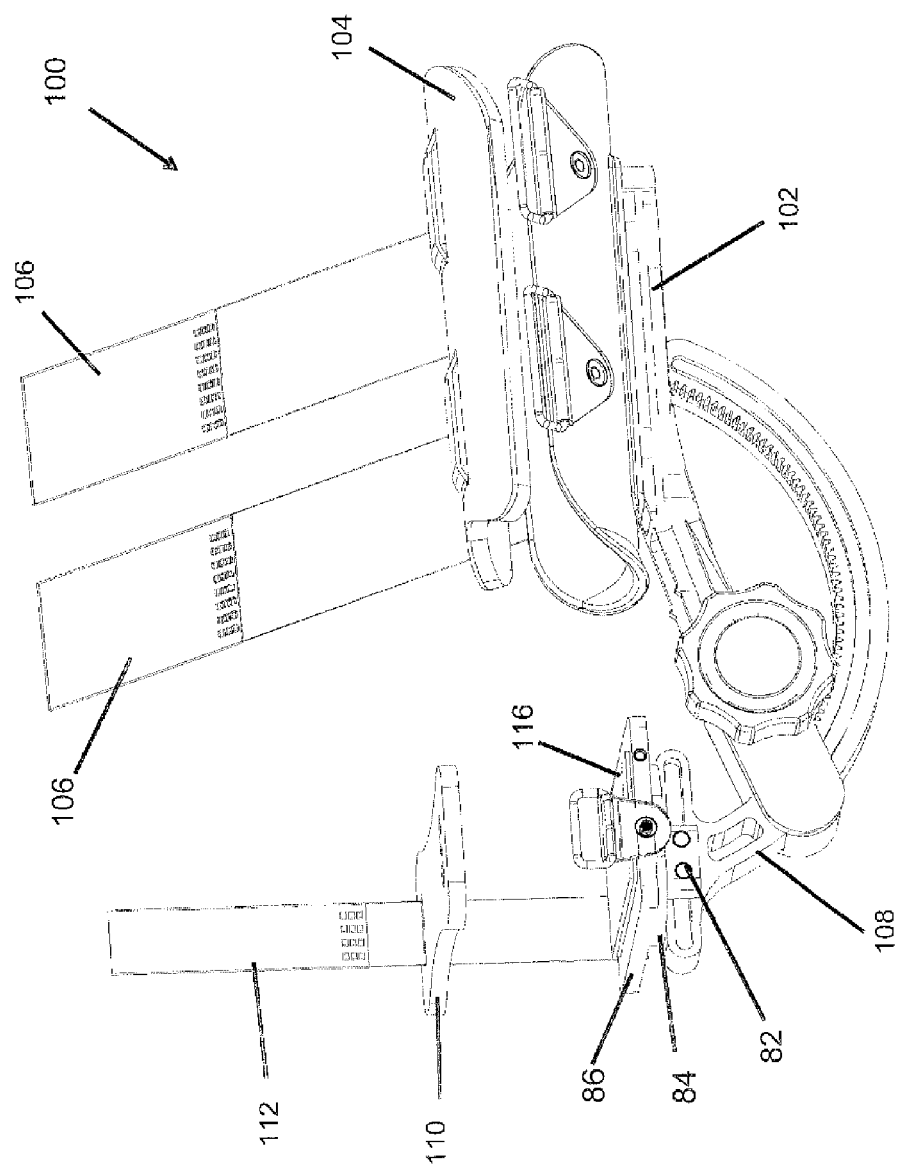
FIG. 18 shows an orthosis of the present invention.

Referring now to FIG. 18, an orthosis 100 can be used to bend a wrist in flexion or extension. The orthosis 100 includes a first arm member 102 attachable to the forearm of a patient. The first cuff 104 is clamped onto the forearm by straps 106. A second arm member 108, operatively connected to the first arm member 102, is attachable to the hand of the patient, wherein the axis of the wrist joint is interposed between and offset from the first and second arm members 102 and 108. The second arm member 108 includes articulating member 80 attached thereto. A hand pad can be attached to the pivotal base plate 86. The hand is clamped onto the hand pad by top member 110 and strap 112, tightly enough so that the second arm member 108 can apply torque to the joint. The hand pad can be shaped to conform to the palm or the back surface of the hand.

Figure 19:
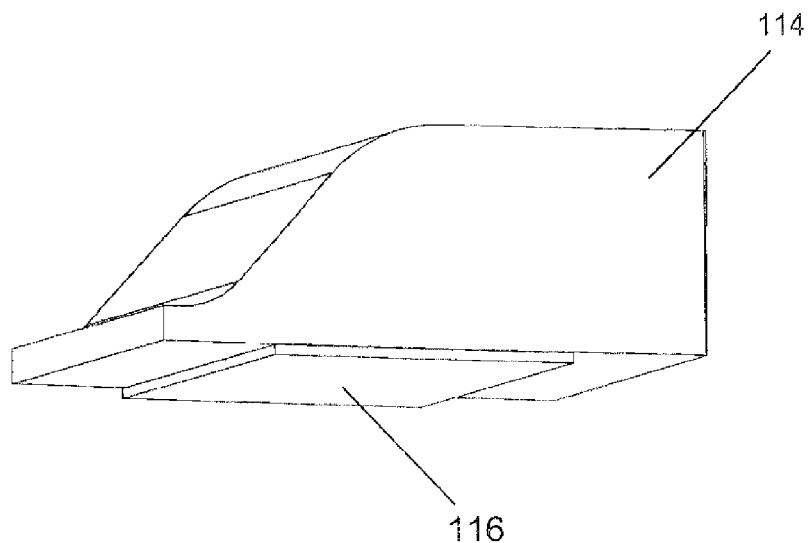
FIG. 19 shows a hand pad for the orthosis of FIG. 18.

Referring to FIG. 19, a hand pad 114 is provided, where the hand pad 114 can be removably attached to the pivotal base plate 86. For example, a hook and loop tape 116 can be provided on the hand pad 114 and the pivotal base plate 86. The hand pad 114 is shaped to conform to the palm of the hand.

Figure 20:
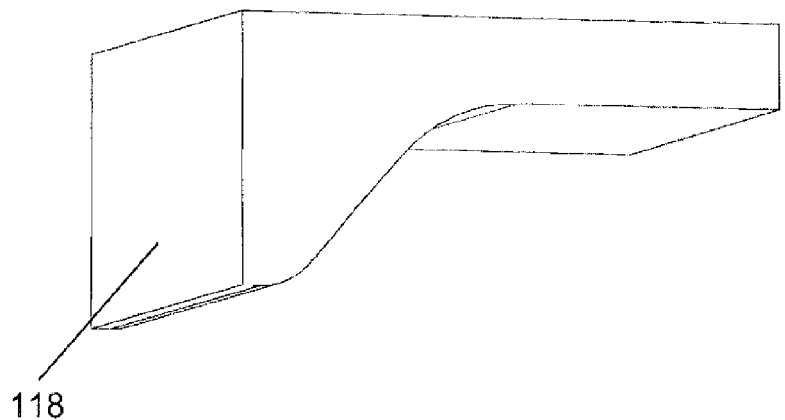
FIG. 20 shows another hand pad for the orthosis of FIG. 18.

Referring to FIG. 20, another hand pad 118 is provided, where the hand pad 118 can be removably attached to the pivotal base plate 86. Similarly, the hook and loop tape 116 can be provided on the hand pad 118 and the pivotal base plate 86. The hand pad 118 is shaped to conform to a top surface of the hand.

Another embodiment of an orthosis of the present invention is in treatment of a toe of a patient's foot. While this embodiment is believed to provide significant improvements in this area of treatment, it may likewise be of benefit in treating other joints, such as ankles, knees, hips, fingers, wrists, elbows, shoulders, or the spine.

Furthermore, while many examples provided herein may illustrate the invention used to treat the metatarsal and proximal phalanx of the toe, these examples are non-limiting on other joints of the toe that also may be treated by the present invention. It is understood by those skilled in the art that the other joints of the toe may be flexed or extended, without departing from the spirit and scope of the invention. Additionally, the present invention is described in use on the "big" toe or hallux on the foot. Thus, it should be understood by those skilled in the art that the present invention is equally applicable for use on the second, third, fourth and minimus toes of the foot.

Each toe in the foot extends from the metatarsal bone and is formed by the proximal phalanx, middle phalanx, and distal phalanx, each of which is respectively pivotally connected to form a joint there between. The orthosis of the present invention may be configured to flex or extend (or both) a toe joint, where the joint defines an inner sector on the flexor side that decreases in angle as the joint is flexed (bent) and an outer sector on the extensor side that decreases in angle as the joint is extended (straightened).

Figure 21:
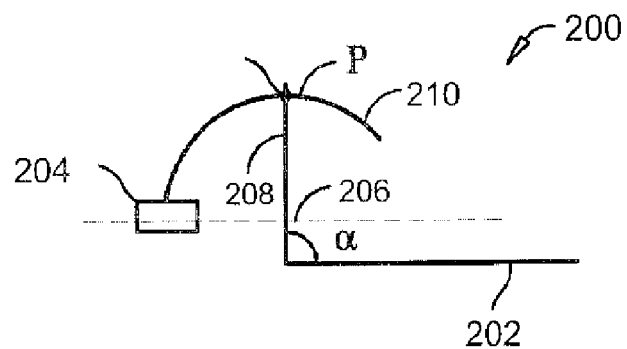
FIG. 21 is a schematic diagram of an orthosis of the present invention.

Referring now to the figures in which like reference designators refer to like elements, there is shown in FIG. 21, a schematic of the orthosis 200 of the present invention. The orthosis 200 includes a first member 202 attachable to a first body portion, such as a user's foot. The shape and configuration of the first member 202 may be selected to support or conform generally to a patient's foot. For example, the first member 202 may be a platform that contacts or supports the underside of a user's foot. Sidewalls or curved edges may be provided to help position, cradle, or securely hold the foot in proper position.

Alternatively, the first member 202 may have a profile or shape that generally conforms to a user's arch, shoe size, or foot width so that it fits more comfortably, holds the foot securely in place, or improves alignment of the device so that the range of motion imparted by the device corresponds to a joint's healthy range of motion. This conforming shape or profile may be accomplished, for instance, by providing interchangeable platforms corresponding to different foot sizes and shapes. The interchangeable platform may be selectively removed and replaced by an interchangeable platform of a different size. Alternatively, the first member 202 may have adjustable surfaces that can be resized or repositioned to better support or correspond to a patient's foot. For example, the overall length of the first member 202 may be adjustable, or the width of the first member 202 near the toes may be adjusted to account for different foot widths. In addition, raised walls or edges that support the feet may be selectively moveable so that they can be moved to accommodate different foot sizes. Once the foot is in place and the edges are moved to their desired position, they may be selectively locked or secured in place to help hold the foot in place. Additionally, the first member 202 may be configured with an arch, which in some instances also may be adjustable such as by having interchangeable arch inserts, by configuring the arch to be inflatable, or the like.

The first member 202 is operatively associated with or connected to a second member 204 so that the first and second members 202 and 204 may move or rotate with respect to each other. As shown in FIG. 21, the supporting surface of the first member 202 may be offset from the supporting surface of the second member 204. This amount of offset provided may vary from patient to patient or from joint to joint, and in some cases an offset may not be provided. Thus, it may be advantageous to allow the offset of the orthosis 200 to be adjustable so that a physician or user may change its size as needed to improve comfort, fit, or operation of the orthosis 200.

Figure 22:
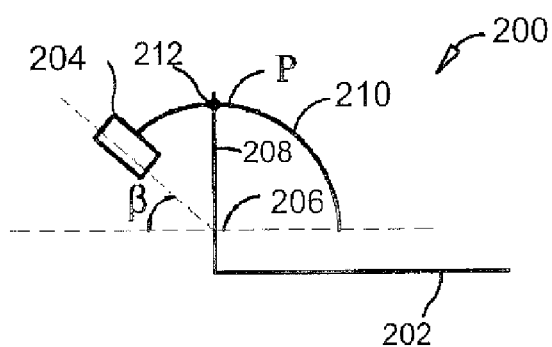
FIG. 22 is a schematic diagram of the orthosis of FIG. 21 in an extended position.
Figure 23:
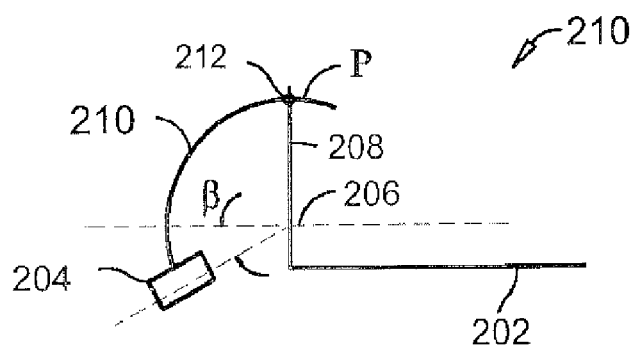
FIG. 23 is a schematic diagram of the orthosis of FIG. 21 in a flexed position.

In use, the second member 204 may be attachable to a second body portion, such as at least one toe on the foot so that the relative movement of the two members also causes movement of the joint. As shown in FIG. 22, the orthosis 200 may have an axis of rotation 206 that is aligned with the axis of rotation of the joint. In this manner, the instantaneous axis of rotation (IAR) of the first and second members 202 and 204 may better match the IAR of the treated joint. As will be discussed in greater detail below, while the axis of rotation 206 of the device is illustrated in FIGS. 21-23 as occurring only along a single line, the axis of rotation 206 may also shift or move depending on the relative positioning of the first and second members 202 and 204 in a manner that corresponds to changing axis of rotation that a joint may experience through its range of motion. The first and second members 202 and 204 are operatively connected to each other, offset from the orthosis axis 206.

The first member 202 of the orthosis 200 includes a first extension member 208 extending therefrom. The second member 204 of the orthosis 200 includes a second extension member 210 extending therefrom and having an arcuate shape. The first and second extension members 208 and 210 are operatively connected at point "P," such that in operation the second extension member 210 travels along an arcuate path about and substantially through point "P." The arcuate shape of the second extension member 210 results in the toe rotating about the orthosis axis 206, or alternatively about a moving IAR, when the second member 204 is moved from a first position to a second position relative to the first member 202.

The first extension member 208 can extend substantially vertically from the first member 12 or extend at an angle α from the first member 202. In one embodiment of the invention, the angle α and the radius of curvature of the second extension member 210 are configured such that of the orthosis axis 206 is aligned with the axis of rotation of the joint.

The previous description of the first member 202 depicts a first extension 208 having a substantially linear shape, extending at an angle α from the first member 202. However, it is within the scope of the present invention that the first extension member 208 can be any shape extending from the first member 202 which aligns orthosis axis 206 with the axis of rotation of the joint. Furthermore, as mentioned previously and again below, in some instances the axis of rotation of the joint may change or move slightly. Therefore, in some instances it may be desirable for the orthosis to mimic the IAR of the joint. As will be illustrated in detail below, this can be accomplished in several ways. One modification of the embodiment of the invention shown in FIG. 21, for instance, may be for the second extension member 210 not to have a constant radius of curvature.

The orthosis 200 further includes a drive assembly 212, which is illustrated in FIG. 21 at or near point "P." In this embodiment, the drive assembly 212 is operably connected to the first and second extension members 208 and 210 for applying force to the first and second members 202 and 204 to pivot the second body portion about the orthosis axis 206. As will be shown below in additional embodiments, the drive assembly 212 may be configured or disposed to interact with or operate on one of the first or second members 202 and 204 independently.

Referring to FIG. 22, in order for the orthosis 200 to extend the joint the first and second members 202 and 204 may be affixed to the first and second body portions, respectively, tightly enough so that the first and second members 202 and 204 can apply torque to extend the joint. The second extension member 210 is moved through the drive assembly 212 from a first position to a second position, relative to the first extension member 208, rotating the second member 204 and the second body portion about the orthosis axis 206 stretching the joint. As the second member 204 is rotated to the second position, the second extension member 210 travels at least partially through point "P" and may travel substantially through this point for a large range of motion. Because the first and second members 202 and 204 are affixed to the first and second body portions, the outward pivoting movement of the second member 204 causes the joint to be extended as desired. The orthosis 200 may then be maintained in the second position for a predetermined treatment time providing a constant stretch to the joint. The orthosis may alternatively be configured to impart a constant force or load on the joint or may utilize the techniques of Static Progressive Stretch as described in co-pending application Ser. No. 11/203,516, entitled "Range of Motion System and Method", and filed on Aug. 12, 2005, the entirety of which is incorporated by reference.

Returning to the example where the orthosis is maintained in the second position, after the expiration of the treatment time, the second member 204 may then be moved back to the first position, relieving the joint. Optionally, the second member 204 can be rotated to a third position, increasing the stretch on the joint, or partially reducing it to allow limited relaxation of the surrounding tissue. The second member 204 can be rotated at discrete time intervals to incrementally increase, reduce, or vary the stretch of the joint through the treatment cycle. After completion of the treatment cycle, the second arm 204 is returned to the first position for removal of the orthosis 200.

Referring to FIG. 23, in operation of the orthosis 200 to flex the joint. The first and second members 202 and 204 are affixed to the first and second body portions, respectively, tightly enough so that the first and second members 202 and 204 can apply torque to extend the joint. A cuff, strap, laces, or other retaining device may be used to securely associate respective body portions of the joint with the first and second members 202, 204. The second extension member 210 is moved through the drive assembly 212 from the first position to a second position, relative to the first extension member 208, rotating the second member 204 and the second body portion about the orthosis axis 206 stretching the joint. As the second member 204 is rotated to the second position, the second extension member 210 travels substantially through point "P." Because the first and second members 202 and 204 are affixed to the first and second body portions, the inward pivoting movement of the second member 204 causes the joint to be flexed as desired. The orthosis 200 is maintained in the second position for a predetermined treatment time providing a constant stretch to the joint.

After the expiration of the treatment time, the second member 204 is moved back to the first position, relieving the joint. Optionally, the second member 204 can be rotated to a third position, thereby increasing, decreasing, or otherwise varying the stretch on the joint. The second member 204 can be rotated at discrete time intervals to incrementally increase the stretch of the joint through the treatment cycle. After completion of the treatment cycle, the second arm 204 is returned to the first position for removal of the orthosis 200.

Figure 24:
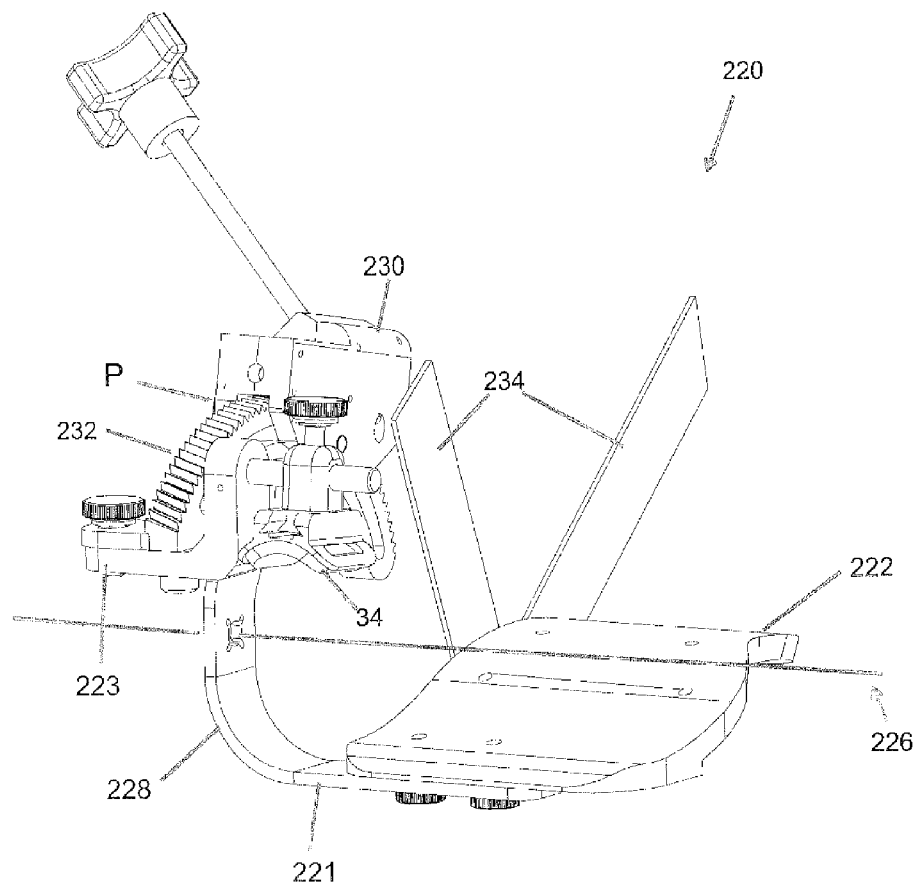
FIG. 24 is an isometric view of an orthosis of the present invention.
Figure 25:
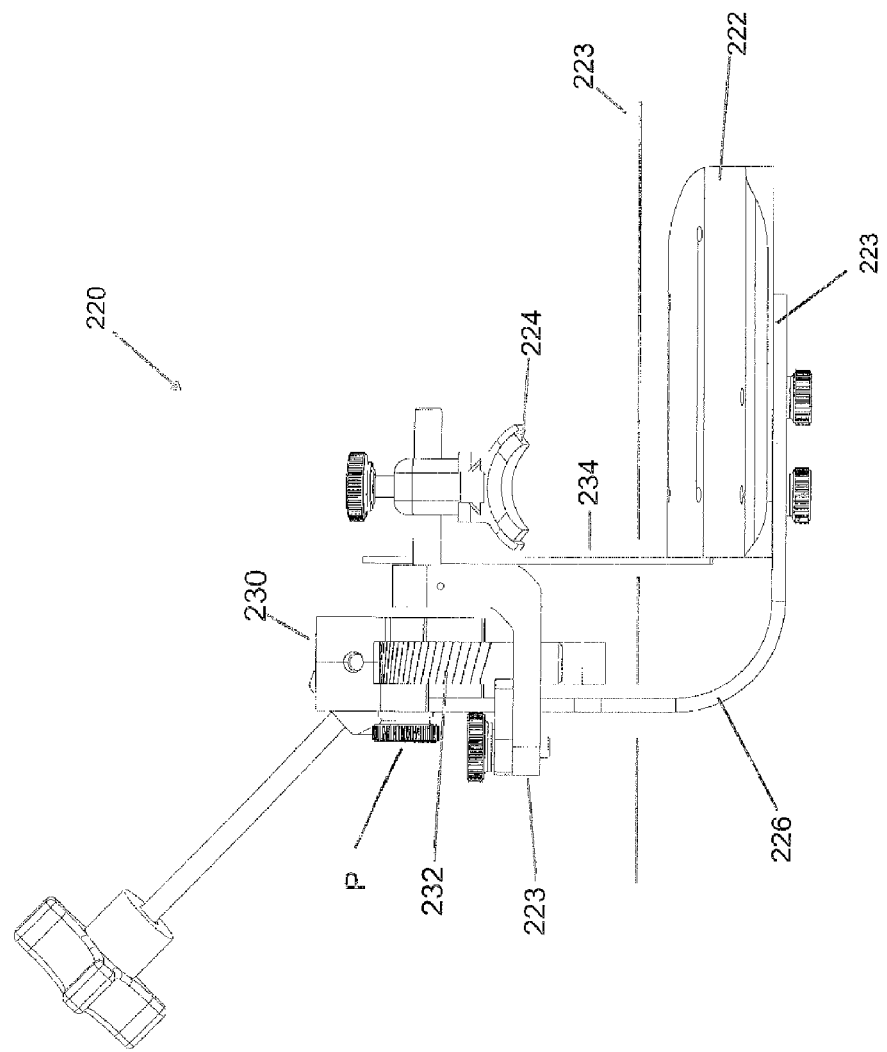
FIG. 25 is a front view of the orthosis of FIG. 24.
Figure 26:
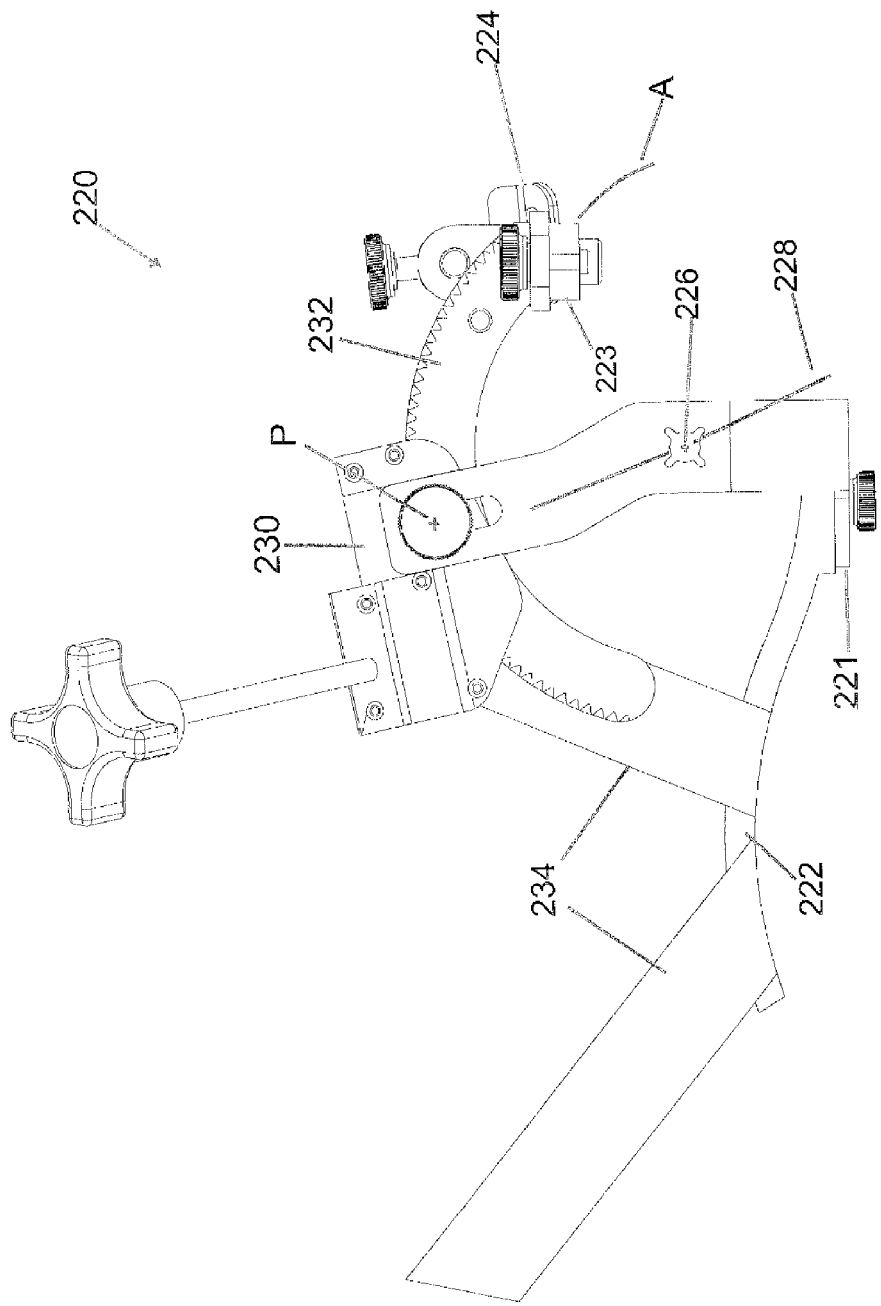
FIG. 26 is a side view of the orthosis of FIG. 24.

FIGS. 24-26 further illustrate several aspects of the invention more concretely. An orthosis 220 of the present invention includes a first member 221 having a first cuff 222 attachable to a user's foot and a second member 223 having a second cuff 224 attachable to a toe of the user's foot, wherein the second member 223 is rotatable with respect to the first member 221 about an axis of rotation 226. The first and second members 221 and 223 are attached to the foot and toe of the user with the first and second cuffs 222 and 224, such that as the second member 223 is rotated about the axis of rotation 226, the toe is rotated about a joint axis.

A first extension member 228 is affixed to and extends from the first member 221, wherein a drive assembly 230 is positioned on an end portion of the first extension member 228. A second extension member 232 is similarly affixed to and extends from the second member 223, wherein the second extension member 232 has an arcuate shape. The second extension member 232 engages the drive assembly 230 of the first extension member 228 at a point "P." An actuation of the drive assembly 230 operates to move the second extension member 232 through the drive assembly 230, such that the second cuff 224 travels along an arcuate path "A" with respect to the first member 221. The arcuate shape of the second extension member 232 results in the toe rotating about the joint axis, as the second cuff 224 is moved along the arcuate path "A." The drive assembly 230 can be actuated to move the second cuff 224 and toe from a first position to a second position relative to the first cuff 222. Once again, the term "cuff" as used herein means any suitable structure for transmitting the force of the orthosis 220 to the limb portion it engages.

The first extension member 228 can extend substantially vertically from the first member 221 or extend at an angle α from the first member 221, where the angle α and the radius of curvature of the second extension member 232 (if constant) can be configured such that of the axis of rotation 226 is aligned with the joint axis of ration. As previously discussed, the curvature of the second extension member 232 need not be constant, and therefore the axis of rotation may shift or move in a manner that preferably mimics or approximates the moving IAR the joint would normally have. Another potential benefit of the orthosis 220 having the capability of a moving IAR is when multiple joints are being treated by the device. For instance, the range of motion of the tip of a toe or finger may involve cooperative motion of two or more joints. If the combined bending of the multiple joints causes the overall motion to rotation about a moving axis, it would be beneficial for the orthosis to approximate this moving IAR. Thus, the curvature of the second extension member 232 may be complex in order to better approximate a moving IAR.

Figure 27:
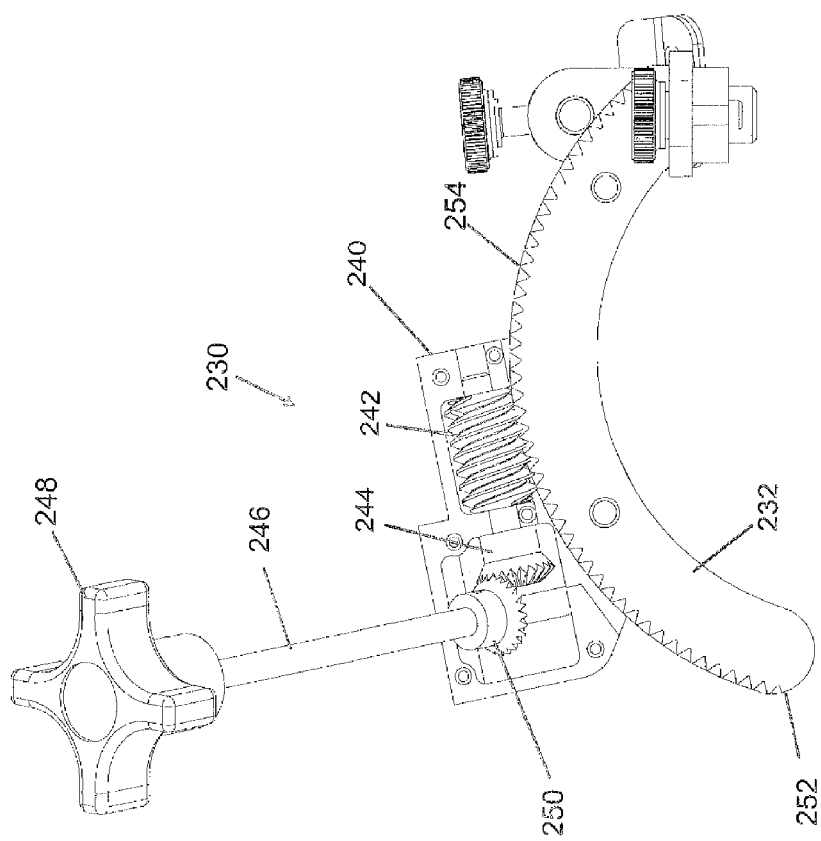
FIG. 27 is a sectional view of a drive assembly of the orthosis of FIG. 24.

Referring to FIG. 27, the drive assembly 230 can include a housing 240 having a worm gear 242 therein. A first miter gear 244 is attached to the worm gear 242 such that a rotation of the first miter gear 244 rotates the worm gear 242. The drive assembly 230 further includes a drive shaft 246 have a knob 248 at one end and a second miter gear 250 at an opposite end. The second miter gear 250 is positioned within the housing 240, in engagement with the first miter gear 244. A rotation of the knob 248 rotates the drive shaft 246 and the second miter gear 250, which in turn rotates the first miter gear 244 and the worm gear 242.

A gear surface 252 of the second extension member 232 includes a plurality of teeth 254. The second extension member 232 is positioned throughout the housing 240, such that the worm gear 242 engages the teeth 254 of the second extension member 232. A rotation of the knob 248 rotates the worm gear 242, which in turn moves the second extension member 232 through the housing 240.

In an alternative embodiment, the drive assembly 230 for orthosis 230 in accordance with the present invention can be actuated by a motor instead of by a manually actuatable member, such as the knob 248. Likewise, the motor may be configured an adapted with gearing that causes the orthosis to cycle through a range of motion in a predetermined manner, or alternatively maybe controlled by a programmable logic controller (PLC).

In an embodiment, an electric motor is mounted to the drive shaft 246 for rotation of the second miter gear 250. A battery or other source of energy provides electric power to the motor. Alternatively, the motor can be supplied with external power. A microprocessor controls the operation of the motor. The microprocessor and motor together can be used to cycle the second cuff 34 through a plurality of positions that cause the joint to undergo a range of motion, either by extension, by flexion, or both. For example, the microprocessor may be used to move the second cuff 34 in one pivotal direction a certain amount, hold there while tissue stretches, then move further in that direction; or in any other manner.

In another manner of use, the orthosis can be set to cycle to one end of the joint's range of motion and hold there for a predetermined period of time, then cycle to the other end of the joint's range of motion and hold there. The programming and control of the microprocessor is within the skill of the art as it relates to driving the motor to control the second cuff 34 to move in known manners. This embodiment is ideally suited for continuous passive motion exercise, because the orthosis is portable and because the motor can be programmed with the desired sequence of movements.

It should be understood that the particular physical arrangement of the motor, the power source, and the microprocessor is not the only possible arrangement of those elements. The invention contemplates that other arrangements of these or similarly functional elements are quite suitable, and thus, the invention is intended to cover any such arrangement. Additionally, another type of power source, other than an electric motor, can also be used. For example, the use of a hydraulic or pneumatic motor as the drive mechanism is contemplated.

The present invention can further include a monitor for use with the orthosis 220, which provides assurances the patient is properly using the orthosis 220 during his/her exercise period. For instance, the monitor can have a position sensor, a temperature sensor, a force sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly.

This analysis may be conducted remotely, thereby saving the time and expense of a home visit by a healthcare professional or technician. An exemplary monitoring system is provided in U.S. Publication No. 20040215111 entitled "Patient Monitoring Apparatus and Method for Orthosis and Other Devices," to Bonutti et al., the content of which is herein expressly incorporated by reference in its entirety.

In an exemplary use, the orthosis 220 is operated to rotate a toe about a joint axis in the following manner. The first cuff 222 is fastened about the foot with one or more straps, laces, or similar retaining device. Similarly, the second cuff 224 is fastened securely to the toe of the user, such that the joint and joint axis 226 is interposed between the first and second cuffs 222 and 224. The orthosis 220 is attached to the foot and toe in a first position. The drive assembly 230 is actuated to move the second extension member 232, such that the second cuff 224 travels along an arcuate path from the first position to a second position, relative to the first cuff 222, rotating the toe about the joint axis stretching the joint. The orthosis 220 is maintained in the second position for a predetermined treatment time providing a constant stretch to the joint. After the expiration of the treatment time, the second cuff 224 is moved back to the first position, relieving the joint. Optionally, the second cuff 224 can be rotated to a third position, thereby increasing or decreasing the stretch on the joint. The second cuff 224 can be rotated at discrete time intervals to incrementally increase the stretch of the joint through the treatment cycle. After completion of the treatment cycle, the second arm member is returned to the first position for removal of the orthosis 220.

Figure 28:
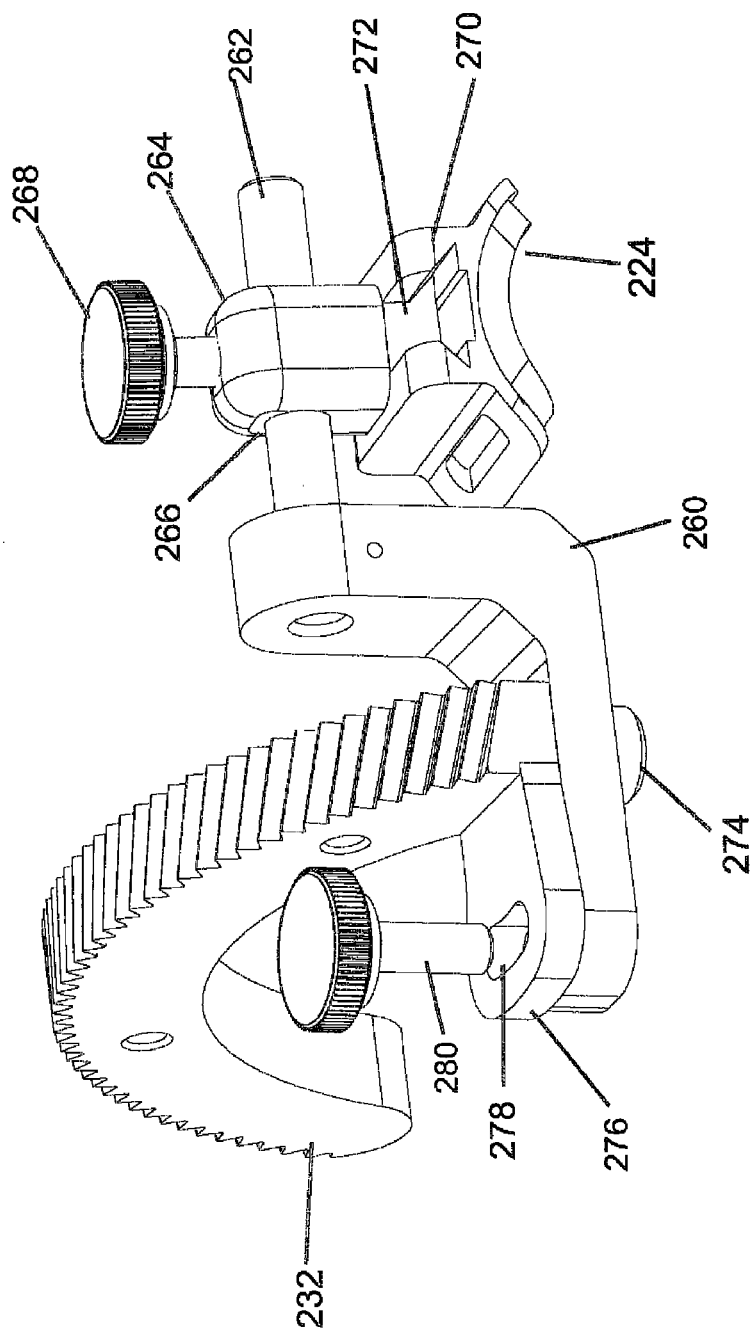
FIG. 28 is a section view of an adjustable second cuff for the orthosis of FIG. 24.

Referring to FIG. 28, the second member 223 can include an attachment bracket 260 for adjustably attaching the second cuff 224 to the second extension member 232. The attachment bracket 260 can include a toe rod 262 extending therefrom. The second cuff 224 can be slideably mounted on the toe rod 262 to position second cuff 224 over the toe. Alternatively, the toe rod 262 can be of sufficient length such that the second cuff 24 can be slidingly positioned on a selected toe on the foot of the user, for example, the big toe, minimus toe, or any toe therebetween.

The second cuff 224 can be positioned on the toe rod 262 with a first bracket 264, where the toe rod 262 passes through a passage 266 in the first bracket 264. A set screw 268 is provided to secure the first bracket 264 to the toe rod 262. When the set screw 268 is loosened, the first bracket 264 is free to slide along the toe rod 262. A tightening of the set screw 268 secures the first bracket 264 in place on the toe rod 272.

The second cuff 224 can further include a second bracket 270, where the second bracket 270 can be pivotally mounted to the first bracket 264. For example, the second bracket 270 can be attached to the first bracket 264 with a pin or screw connector, allowing the second bracket 270 to rotate with respect to the first bracket 264.

Additionally, when a joint is flexed or extended a compressive force may be applied to the connective tissue surrounding the joint. It may be desirable to control the compressive force, distracting the joint as the joint is flexed or extended. "Distraction" is defined by one dictionary as "Separation of the surfaces of a joint by extension without injury or dislocation of the parts." (Taber's Cyclopedic Medical Dictionary, 16th Edition, 1989, page 521), and involves stretching rather than compressing the joint capsule, soft tissue, ligaments, and tendons.

Additionally, the second bracket 270 can be slideably mounted to the first bracket 264. For example the second bracket 270 can be mounted to the first bracket 264 with a dovetail joint 272, allowing the second bracket 270 to slide with respect to the first bracket 264. The sliding movement of the second cuff 224 helps to limit the distractive or compressive forces which can be imparted on the joint by the rotation of the second cuff 224 with respect to the first cuff 222.

The attachment bracket 260 can be pivotally mounted to the second extension member 232. For example, the attachment bracket 260 can be attached to the second extension member 232 with a pin or screw connector 274, allowing the attachment bracket 260 to rotate with respect to the second extension member 232. The second extension member 232 further includes an extension bracket 276 having a slotted portion 278. A set screw 280 is positionable through the slotted portion 278, engaging the attachment bracket 260, such that the set screw 280 can be used to control the pivotal position of the attachment bracket 260 with respect to the second extension member 232.

The adjustable connection of the second cuff 224 to the attachment bracket 260 and the pivotal connection of the attachment bracket 260 to the second extension member 232 can be used to align the second cuff 224 with the toe. The alignment of the second cuff 224 on the toe can be used to substantially limit the force applied to the toe to that of a torque about the joint axis 226.

Bending a Joint in Extension:

In operation of the orthosis 220 to extend the joint, the orthosis starts at a more flexed position. The first and second cuffs 222 and 224 are clamped onto the foot and toe portions, respectively, by straps 234, tightly enough so that the first and second members 221 and 223 can apply torque to extend the joint. The second extension member 232 is moved through the drive assembly 230 from the first position to a second position, relative to the first extension member 228, rotating the second cuff 224 and the toe about the orthosis axis 226 stretching the joint. As the second cuff 224 is rotated to the second position the second extension member 232 travels along an arcuate path "A" about and substantially through point "P." The orthosis 220 is maintained in the second position for a predetermined treatment time providing a constant stretch to the joint.

As the orthosis 220 is rotated from the first position to the second position, extending the joint, the second cuff 224 moves along the first bracket 64. Because the first and second members 221 and 223 are clamped onto the foot and toe as described above, the outward pivoting movement of the second cuff 224 causes the joint to be extended as desired. However, this extension of the joint can place strong distractive forces on the soft tissues around the joint. The sliding movement of the second cuff 224 helps to limit these distractive forces by counteracting the outward movement. Thus, the detrimental effects of strong distractive forces normally generated in forced extension of a joint are avoided, being replaced with the beneficial effects of limited and controlled distraction.

Bending a Joint Flexion:

In operation of the orthosis 220 to flex the joint, the orthosis 220 starts at a more extended position. The first and second cuffs 222 and 224 are clamped onto the foot and toe portions, respectively, by straps 234, tightly enough so that the first and second members 221 and 223 can apply torque to extend the joint. The second extension member 232 is moved through the drive assembly 230 from the first position to a second position, relative to the first extension member 228, rotating the second cuff 224 and the toe about the orthosis axis 26 stretching the joint. As the second cuff 224 is rotated to the second position the second extension member 232 travels along an arcuate path "A" about and substantially through point "P." The orthosis 220 is maintained in the second position for a predetermined treatment time providing a constant stretch to the joint.

As the orthosis 220 is rotated from the first position to the second position, flexing the joint, the second cuff 224 moves along the first bracket 264. Because the first and second members 221 and 223 are clamped onto the foot and toe as described above, the inward pivoting movement of the second cuff 224 causes the joint to be flexed as desired. However, this flexion of the joint can place strong compressive forces on the soft tissues around the joint. The sliding movement of the second cuff 224 helps to limit these compressive forces by counteracting the inward movement. Thus, the detrimental effects of strong compressive forces normally generated in forced flexion of a joint are avoided, being replaced with the beneficial effects of limited and controlled compression.

Figure 29:
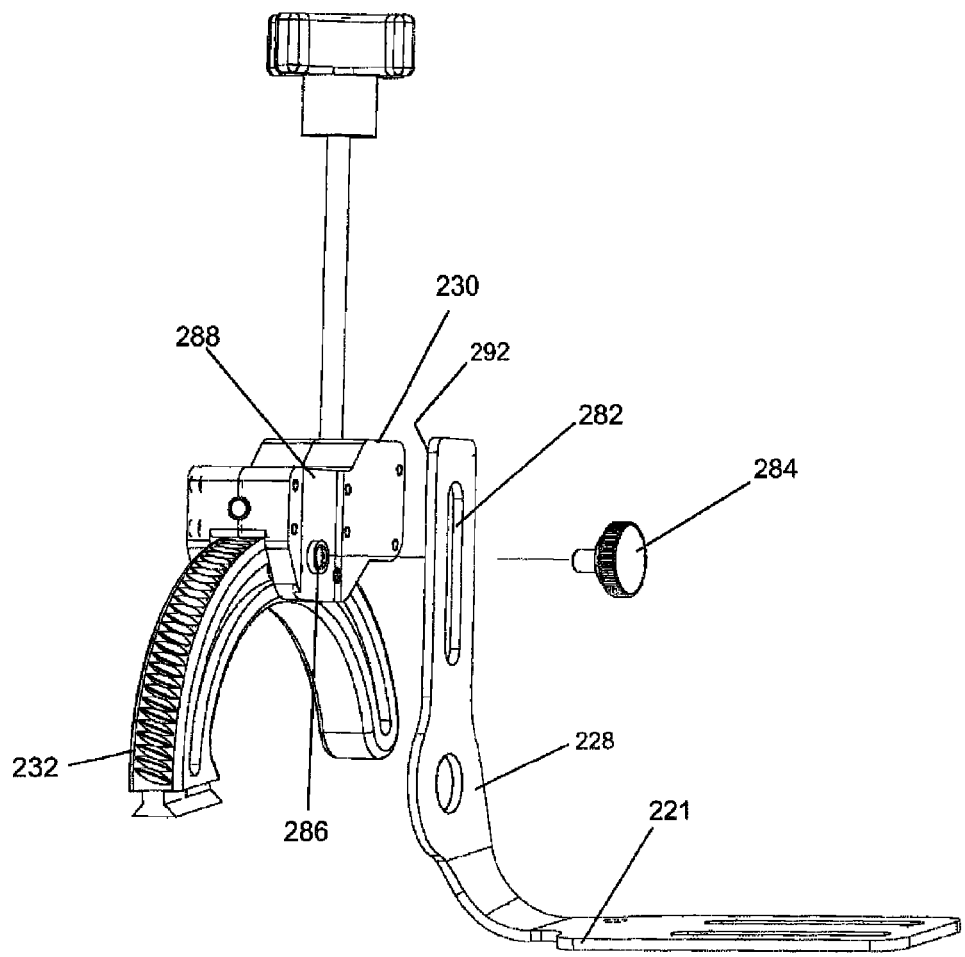
FIG. 29 is an expanded view of the drive assembly connection to the first member of the orthosis of FIG. 24.

Referring to FIG. 29, the drive assembly 230 can be adjustable mounted to the first extension member 228. The first extension member 228 includes a longitudinal slotted section 282. A threaded member 284 is positioned through the longitudinal slotted section 282, where the threaded member 284 is threaded into a threaded hole 286 in the drive assembly 230. The position of the drive assembly 230 is secured on the first extension member 228 by tightening the threaded member 284, compressing the first extension member 228 between the threaded member 284 and the drive assembly 230. The position of the drive assembly 230 can be adjusted by loosening the threaded member 284 and sliding the drive assembly 230 along the longitudinal slot 282. In this manner the position of the drive assembly 230 can be adjusted to align the axis of rotation 226 with the joint axis.

The drive assembly 220 can further includes an indented portion 288. The indented portion 288 in sized to receive the first extension member 228 therein, such that the first extension member 228 slides through the indented portion 288 as the drive assembly 230 is moved along the first extension member 230. The indented portion 288 is configured to align the drive assembly 230 with respect to the first extension member 228. The indented portion 288 provides the further benefit of resisting a rotation of the drive assembly 230 with respect to the first extension member 228 when the orthosis 220 is in use.

Figure 30:
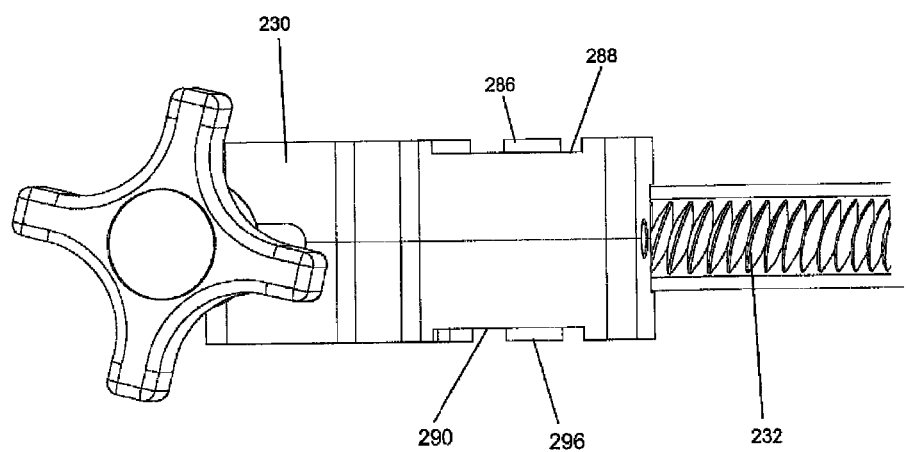
FIG. 30 is a top view of the drive assembly of the orthosis of FIG. 24.

Referring to FIG. 30, the drive assembly 230 can include a pair of indented portions 288 and 290, positioned on opposite sides on the drive assembly 230. As shown in FIG. 29, the first indented section 288 can be used to position the drive assembly 230 in an outer position on the orthosis 220, where the drive assembly 230 is positioned on an outside surface 292 of the first extension member 228.

Figure 31:
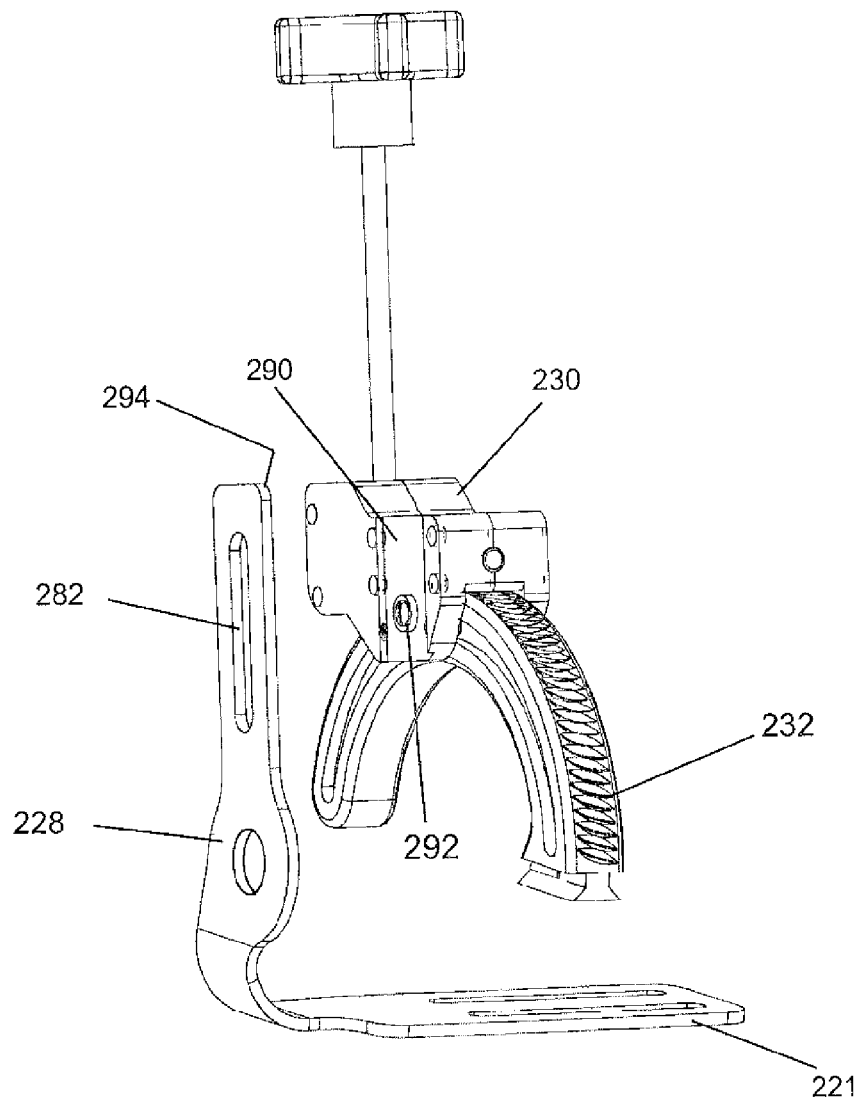
FIG. 31 is an expanded view of another drive assembly connection to the first member of the orthosis of FIG. 24.

Alternatively, as shown in FIG. 31, the second indented section 290 can be used to position the drive assembly 230 in an inner position on the orthosis 220, where the drive assembly 230 is positioned on an inner surface 294 of the first extension member 228. The threaded member 284 is positioned through the longitudinal slotted section 282, where the threaded member 284 is threaded into a second threaded hole 296 in the drive assembly 230.

In an embodiment, the first member 221 can be adjustable mounted to the first cuff 222, such that the position of the second cuff 224 can be adjusted to align the second cuff 224 with a toe of interest and the joint axis of the toe. In instances were the joint of a toe is misaligned, for example for toe deformations such as hammer toe, bunion, etc, the linear and angular position of the second cuff 224 can be adjusted with respect to the first cuff 222 aligning the second cuff 224 with the misaligned toe such that the axis of rotation 226 of the orthosis 220 is aligned with the axis of rotation of the toe joint. In the manner, the orthosis 220 can be adjusted to prevent the unwanted application of torsional forces to the toe joint.

Figure 32:
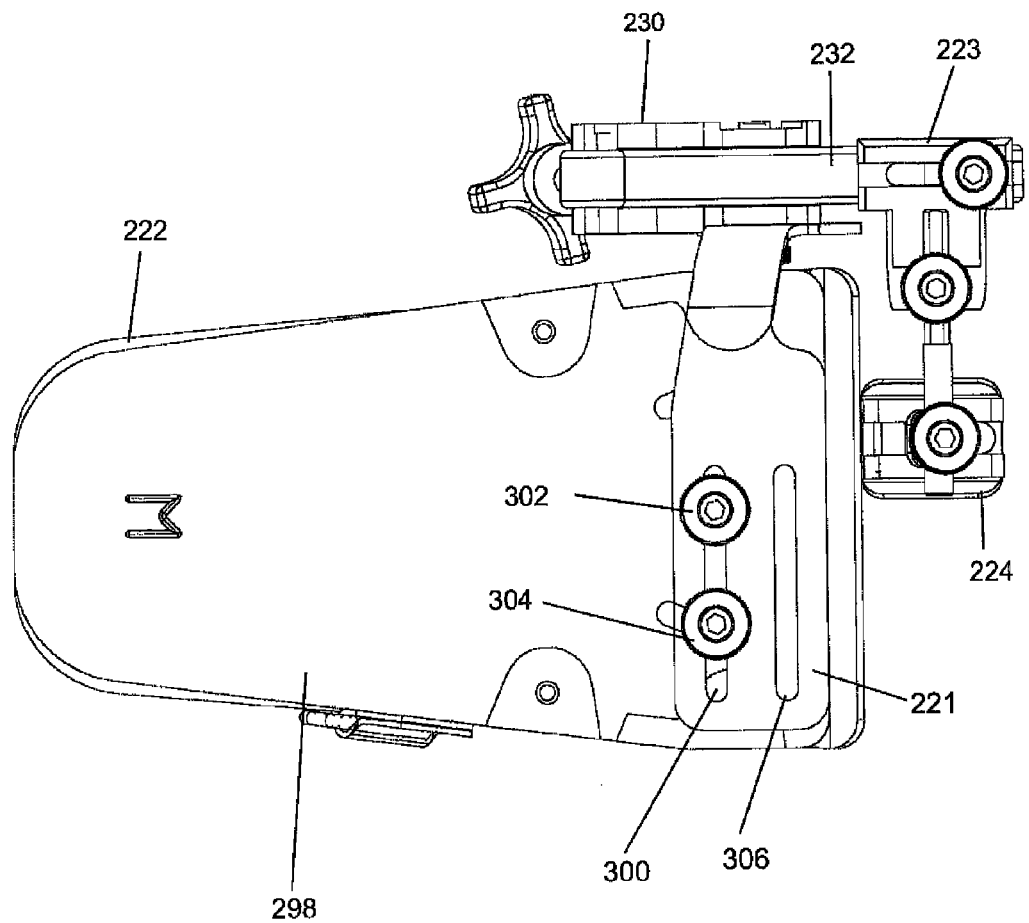
FIG. 32 depicts a bottom view of the orthosis of FIG. 24.

Referring to FIG. 32, the first member 221 is adjustably attached to a bottom surface of the first cuff 222. The first member 221 can included a longitudinal slot 300, through which a pair of threaded members 302 and 304 are positioned, attaching the first member 221 to the first cuff 222. The first member 221 can be moved along the longitudinal slot 300 to laterally adjust the position of the first member 221 with respect to the first cuff 222. The first member 221 is secured in position by tightening the threaded member 302 and 304, compressing the first member 221 between the threaded members 302 and 304 and the bottom surface 298 of the first cuff 222.

The first member 221 can further include a second longitudinal slot 306, parallel and offset from the first longitudinal slot 300. The first member 221 can be attached to the first cuff 222, using the second longitudinal slot 306 to longitudinally adjust the position of the first member 221 with respect to the first cuff 222. Similarly, the first member 221 can be moved along the second longitudinal slot 306 to laterally adjust the position of the first member 221 with respect to the first cuff 222.

Figure 33:
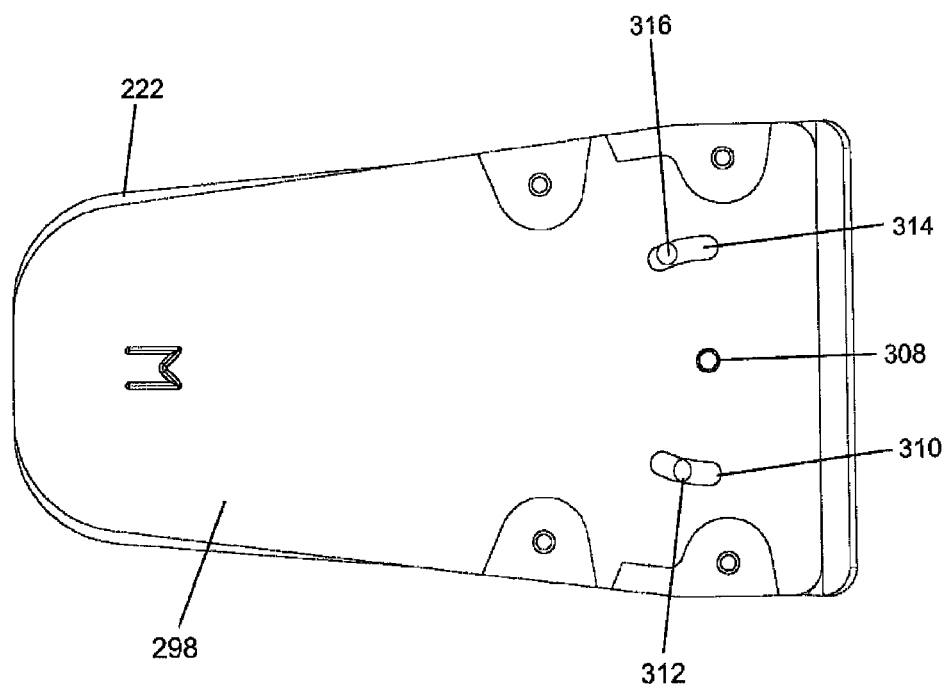
FIG. 33 depicts a bottom view of a first cuff of the orthosis of FIG. 24.

It is also contemplated that the angular position of the first member 221 can be adjusted with respect to the first cuff 222. In an embodiment, as shown in FIG. 33, the bottom surface 298 of the first cuff 222 includes a center threaded hole 308 and an arcuate slot 310. An internally threaded fastener 312 is slidingly positioned in the arcuate slot 310, opposite the bottom surface 298. The first member 221 is attached to the first cuff 222 by positioning the threaded members 302 and 304 through a longitudinal slot 300 or 306 of the first member 221 and engaging the threaded hole 308 and the internally threaded fastener 312 in the arcuate slot 310. The angular position of the first member 221 can be adjusted with respect to the first cuff 222 by pivoting the first member 221 about threaded member 302 in the center threaded hole 308, such that the internally threaded fastener 312 and the second threaded member 302 travel along the arcuate slot 310. The first member 221 is secured in position by tightening the threaded members 302 and 304, compressing the first member 221 between the threaded members 302 and the bottom surface 298 of the first cuff 222, and compressing the first member 221 and first cuff 222 between threaded member 304 and internally threaded fastener 312.

The bottom surface 298 of the first cuff 222 can further include a second arcuate slot 314, where an internally threaded fastener 316 is slidingly positioned in the second arcuate slot 314, opposite the bottom surface 298 of the first cuff 222. Similar to arcuate slot 310, second arcuate slot 314 can be used to angularly adjust the position of the first member 221 with respect to the first cuff 222.

Specifically, the first member 221 is attached to the first cuff 222 by positioning the threaded members 302 and 304 through a longitudinal slot 300 or 306 of the first member 221 and engaging the threaded hole 308 and the internally threaded fastener 316 in arcuate slot 314. The angular position of the first member 221 can be adjusted with respect to the first cuff 222 by pivoting the first member 221 about threaded member 302 in the center threaded hole 308, such that the internally threaded fastener 316 and the second threaded member 304 travel along the arcuate slot 314. The first member 221 is secured in position by tightening the threaded member 302 and 304, compressing the first member 221 between the threaded members 302 and the bottom surface 298 of the first cuff 222, and compressing the first member 221 and first cuff 222 between the threaded member 304 and internally threaded fastener 316.

It is also contemplated that the first member 221 can be attached to the first cuff 221 using the arcuate slots 310 and 314 and the respected internally threaded members 312 and 316. Specifically, the first member 221 is attached to the first cuff 222 by positioning the threaded members 302 and 304 through a longitudinal slot 300 or 306 of the first member 221 and engaging the internally threaded fastener 312 in the arcuate slot 310 and the internally threaded fastener 316 in arcuate slot 314. The angular position of the first member 221 can be adjusted with respect to the first cuff 222 by pivoting the first member 221 such that the internally threaded fasteners 312 and 316 travel along the arcuate slots 310 and 314. The first member 221 is secured in position by tightening the threaded member 302 and 304, the first member 221 and first cuff 222 between the treaded members 302 and 304 and internally threaded fastener 312 and 316.

While the embodiment discussed above utilize a second extension member having an arcuate shape to control movement of the second member relative to the first, it should be understood that skilled artisans having the benefit of this disclosure will appreciate that other configurations may likewise provide similar relative movement.

Figure 34:
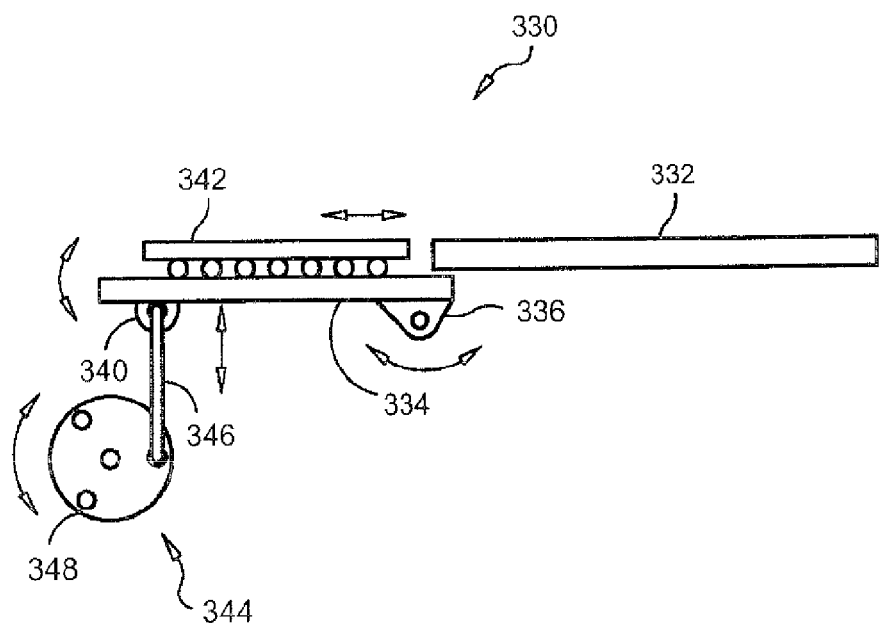
FIG. 34 is a schematic diagram of an embodiment of an orthosis of the present invention.

FIG. 34, for example, schematically illustrates an embodiment of an orthosis 330 of the invention having a first member 332 and a second member 334, both of which preferably having sufficient structure or component parts to hold body members near the treated joint or joints. In the embodiment illustrated in FIG. 34 the second member has a first pivoting contact point 336 about which the geared body member may rotate. In this embodiment, the first pivoting contact 336 does not move in relation to the first body member 330, but as indicated in FIG. 32 one alternative embodiment may allow relative movement that can be resisted by a flexible device 338 such as a spring, compressed gas, foamed material, elastomer or the like.

Returning once again to FIG. 34, the second member may have an additional pivot contact 340, preferably disposed at a location at or near the opposite end of the second member 334 from where the first pivoting contact 336 is located. The second pivoting contact 340 may be configured with a drive assembly 344 that causes the second member 334 to follow a predetermined path. Thus, the second pivoting contact 340 in the embodiment of FIG. 34 is configured to move relative to the first member 332 in order to cause the joint to move from a first position to second one.

The drive assembly 344 illustrated in FIG. 34 is an arm or linkage 346 connected between the second pivot connection 340 and a rotating wheel 348. The wheel 348 may be configured so that the linkage 346 can be selectively connected to it in different radial distances from the center of rotation of the wheel. This allows the range of motion to be adjustable by the care provider, physician, or patient. As the wheel 348 is rotated, the linkage 346 moves in a manner that causes the second member 334 to move in a particular way.

The second member 334 (or alternatively the first member 332) may also have a sliding contact surface 342. The sliding contact surface 342 allows the joint to rotate or move according to its natural instantaneous axis of rotation. Thus, if the second pivot contact 340 moves in a manner that does not always exactly correspond to the axis of rotation of the joint, the sliding contact surface 342 may move or adjust accordingly. Another potential advantage of the sliding contact surface 342 is that is may help facilitate proper alignment of the joint in the orthosis during initial setup.

FIG. 34 illustrates some variations that may also be used in orthosis of the invention. For instance, the first and or second pivot contact may be configured with a cushion or spring 338 that allows one or both ends of the second member to impart some flexibility in the force imparted to the joint. As noted above, the cushion or spring 338 may be made of a variety of suitable materials and constructions to permit some flexibility in the movement of the pivot points 336, 340.

The use of a spring or cushion allows the orthosis 330 to be used in different treatment protocols than just by holding the joint in a prescribed location for a period of time. Instead, the orthosis can utilize the principles of static progressive stretch as described in copending application Ser. No. 11/203,516, entitled "Range of Motion System and Method", and filed on Aug. 12, 2005, the entirety of which is incorporated by reference.

Figure 35:
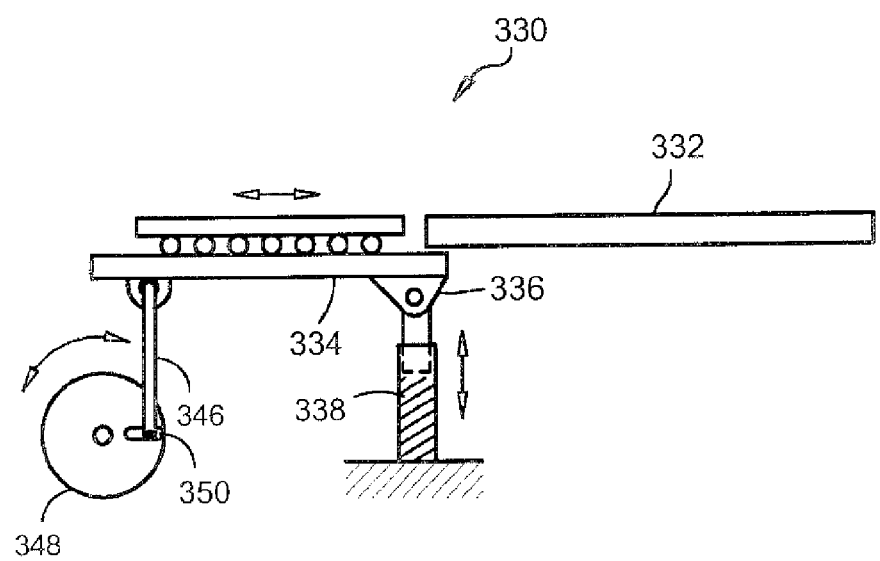
FIG. 35 illustrates another embodiment of the invention utilizing a cushion or spring.

Thus, an orthosis 330 configured with a spring or cushion 338 can be moved from an initial position to a second position that is determined not by position of the joint but instead by the amount of force the orthosis 330 imparts on the joint. The joint may then be subjected to this loading, and over time as the surrounding tissue stretches the joint will move and the imparted forces will be reduced. It should be noted that while FIG. 35 illustrates the cushion or spring 338 associated with the first pivot contact 336, it is not required to be associated with it. Instead, for example, the cushion or spring 338 may be associated with the second pivot 340 so that it can flex or move in response to resistive forces of the joint and nearby tissue. Likewise, there may be a spring or cushion 338 associated with both pivot contacts 336, 340.

Another notable variation between the embodiments of FIGS. 34 and 35 is that the rotating wheel 348 in FIG. 34 has multiple single point connections for connecting the linkage 346 at different distances from the center of rotation of the wheel. In contrast, the embodiment of FIG. 35 illustrates that an elongated slot 350 may be used to connect the linkage 346. The advantage of utilizing multiple single point connections may be ease of use and the ability to quickly confirm the orthosis 330 is properly configured for a prescribed treatment protocol, whereas one potential advantage of utilizing an elongated slot 350 is the ability to quickly adjust the settings without disassembling the device.

Figure 36:
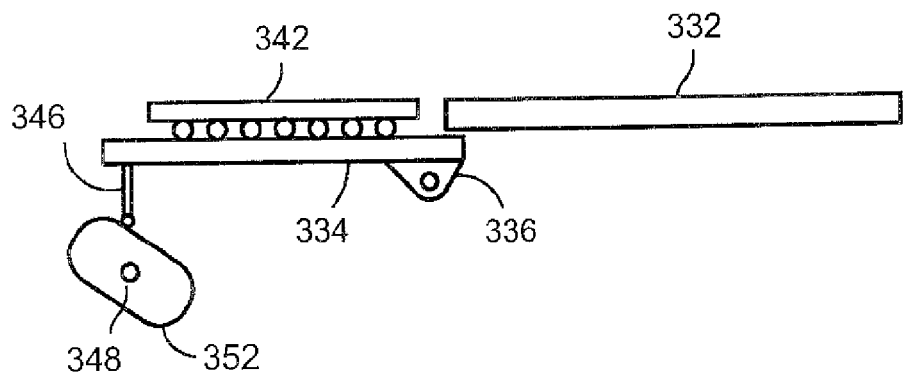
FIG. 36 is an embodiment of the invention illustrating the use of a cam surface.

FIG. 36 illustrates an embodiment of the invention where the rotating wheel 348 is a cam surface 352. This embodiment is similar to the use of cams and followers as described in U.S. Pat. No. 5,514,143, which is incorporated herein in its entirety. As shown, the cam surface 352 may have varying distance from the center or rotation of the wheel 348. If the wheel 358 is circular, for example, the center of rotation may be located somewhere different from the geometric center of the circle or at the center or rotation of the shape. As it rotates, the circumferential outer surface causes the linkage 346 to move to the second member 340 in a desired manner. Additionally, the outer edge of the "wheel" 348 need not be round, but instead may be a cam surface 352 of varying distance from the center or rotation. Likewise, the outer surface may have varying radii of curvature as shown in FIG. 36.

Figure 37:
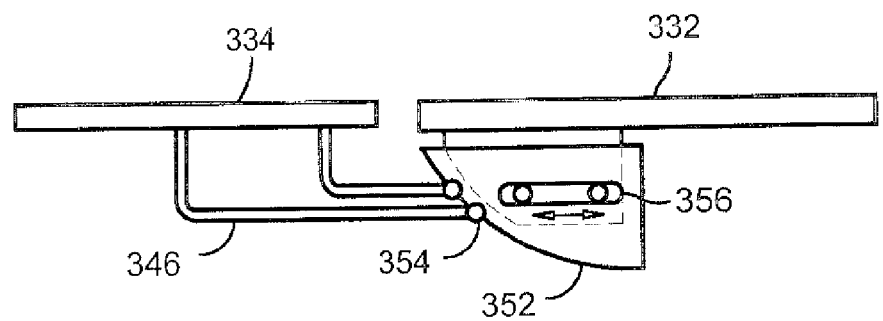
FIG. 37 is an embodiment of the invention utilizing a slideable arcuate surface.
Figure 38:
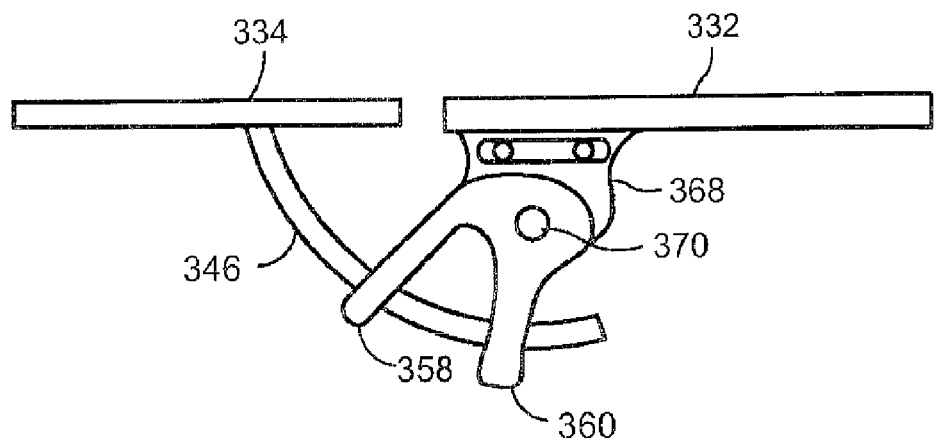
FIG. 38 illustrates features of an orthosis of the invention where the relative positions of component parts of the orthosis are adjustable.

The embodiments of FIGS. 37 and 38 further illustrate that a cam surface 352 may be used to move the second member 332 in a desired, perhaps complex way. As is the case for other embodiments described herein, performance of the cam surface 352 may be enhanced because of the ability to better mimic or replicate a moving axis of rotation of the treated tissue and joint.

In FIG. 37, the cam surface 352 is associated with the first member 332. Linkages or arms 346 of the second member 334 have cam followers 354 that trace the cam surface 352 and cause the second member 334 to move in a more complex manner than just by rotation around a fixed axis.

The cam surface 352 of FIG. 37 also is associated with a slot 356 that allows the relative location of the first and second members 332 and 334 to be adjusted or moved without decoupling the cam followers 354 from the cam surface 352. As shown, the slot 356 allows for horizontal adjustment repositioning. Although not shown, vertical slots may also be provided, either alone or in combination with a horizontal slot.

FIG. 38 illustrates an example where the linkage 346 is a cam surface 352 that passes through two or more points 358, 360 that are stationary or fixed relative to the first member 332 when the orthosis 330 is in use (i.e. after alignment is completed). Once again, this embodiment may be configured to permit horizontal adjustment, such as by providing slot 368, and likewise may be configured to be vertically adjustable. In addition, this embodiment also illustrates that the first and second members 332 and 334 may be represented by rotation about a pivot 370. Thus, the use of horizontal, vertical, and rotational adjustment of the relative positions of the first and second members 332 and 334 may allow greater fitting of the orthosis 330 to the treated tissue and joint.

Figure 39:
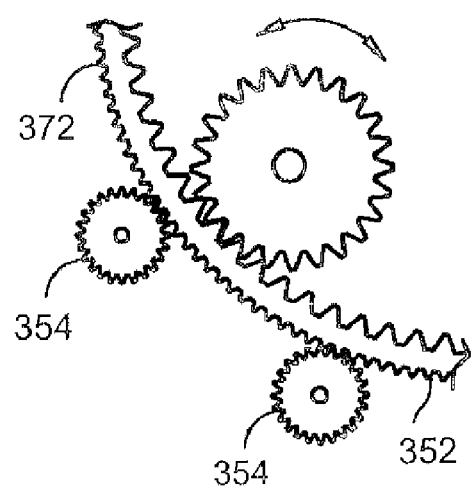
FIG. 39 is an illustration of the use of gears with an arcuate or cam surface of an orthosis of the invention.

FIG. 39 is an exploded view of how the cam surface 352 and cam followers 354 may utilize a geared surface 372. Utilizing a geared surface 372 may allow for a drive assembly 344 to automate the movement of the orthosis 330.

Figure 40:
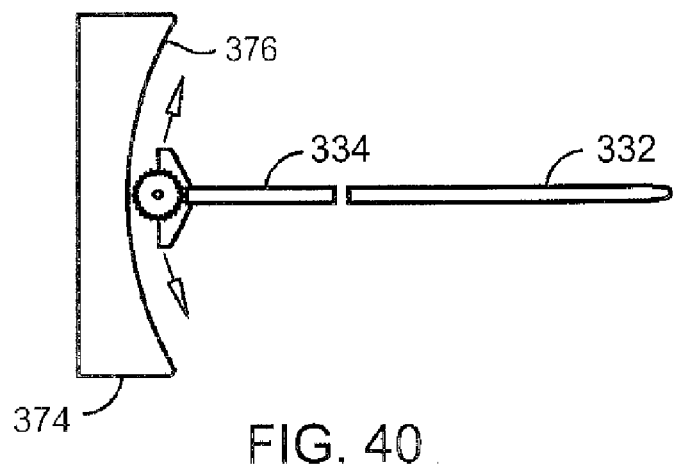
FIG. 40 is a schematic diagram of an embodiment of the invention using an arcuate path and gear or cam follower.
Figure 41:
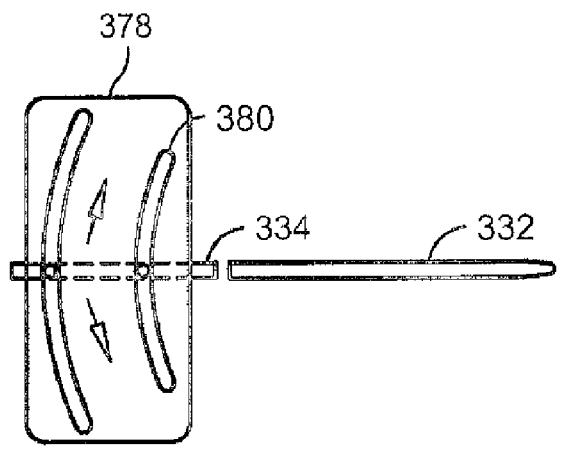
FIG. 41 illustrates the use of a multi-slotted component to control movement of the orthosis.

FIGS. 40 and 41 schematically illustrate other ways in which potentially complex movement of the second member 334 may be controlled. FIG. 40 illustrates that the cam surface may not be directly formed from a component part of either the first or second members, but instead maybe associated with some other structure. For instance, the orthosis 330 may be operatively connected to a base unit 374 having a plurality of cam surfaces 376 corresponding to different ranges of motion for related joints, such as when the orthosis 330 can be used to treat a plurality of different toes or a patient. Once the orthosis 181 is placed on the patient, the second member 334 will be positioned to securely hold one of the toes on the patient's foot and to engage with the cam surface 376 corresponding to that toe.

FIG. 41 shows that multiple cam surfaces or slots 378 may be formed in a side panel 380. The side panel 380 may have a sliding engagement of the second member 334. As the second member 334 moves, the engagement with the side panel 380 controls position and movement. Moreover, one or more sides or edges of a slot 316 of the embodiment of FIG. 41 may be geared to allow implementation of a drive assembly 344.

Figure 42:
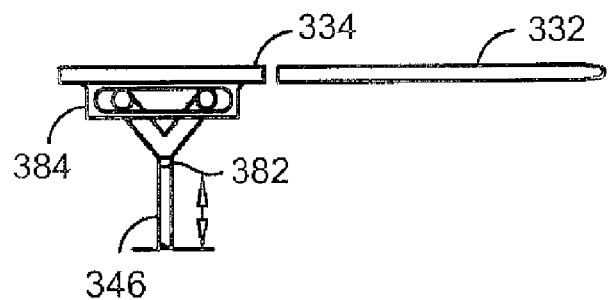
FIG. 42 illustrates an embodiment of the invention where linear movement of a component is translated into rotational and translational movement of another component of the orthosis.

FIG. 42 illustrates an embodiment where movement of at least part of a linkage 346 may be linear, but when combined with a rotational pivot 382, sliding slot 384, and possibly other components or combinations described herein, the net effect on the second member 334 is once again a controlled movement in a desired manner.

The components of the present invention are rigid members made of, for example, aluminum, stainless steel, polymeric, or composite materials. The member and extensions are sufficiently rigid to transmit the necessary forces. It should be understood that any material of sufficient rigidity might be used. For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

In a method of manufacture, the cuffs can include a base plate having a plurality a strap attached thereto, where the straps are position about a body portion of a patient. The straps are attached to the base plate using fastener elements, such as screws threaded into the base plate. The screws can be removable to allow for easy removal and/or replacement of the straps.

Alternatively, in an embodiment where the base plate is made of a polymeric material, the straps can be welded to the base plate using an energy welding technique such as, RF welding, ultra-sonic welding, high frequency welding, etc. For example, in ultra-sonic welding an acoustic tool in used to transfer vibrational energy into the weld areas of the straps and the base plate. The friction of the vibrating molecules generates heat, which melts the surface material of the base plate in the welding area, at which point the vibrational energy is stopped. Pressure is applied to the strap and the base plate, allowing the melted material to solidify within the material of the strap. In this method the strap is secured to the base plate without the need of fasteners.

Similarly, where the cuffs are made of a polymeric material, the cuff can be welded to the orthosis using energy welding techniques. For example, the cuffs can be made of a substantially rigid, flexible, or fabric polymeric material which can be welded directly onto the arm members of the orthosis. It is also contemplated that the straps can be an integral part of the cuffs. For example, where the cuffs are made of a polymeric fabric, the straps can be integrally formed in the fabric pattern when making the cuffs.

All references cited herein are expressly incorporated by reference in their entirety.

It will be appreciated by persons skilled in the art that the present invention is not limited to what has been particularly shown and described herein above. For example, although the examples presented identify the toe joint, the present invention can be used for any joint in the body of the patient. In addition, unless mention was made above to the contrary, it should be noted that not all of the accompanying drawings are to scale. A variety of modifications and variations are possible in light of the above teachings without departing from the scope and spirit of the invention, which is limited only by the following claims.

What is claimed:

1. A device for flexing tissue about a joint of an arm of a wearer, the device comprising:
   a first arm member including a first extension member;
   a sliding contact surface configured to couple to a first arm portion of the wearer and configured to translate along the first arm member;
   a second arm member including a second extension, the second arm member configured to couple to a second arm portion of the wearer; and
   a drive assembly coupled to the first and second arm members and configured to move the first arm member in an arcuate path.

2. A device according to claim 1, further comprising a resistive member configured to at least one of resist and provide relative movement of the first arm member.

3. A device according to claim 2, wherein the resistive member is a spring.

4. A device according to claim 2, wherein the resistive member has resistance provided by at least one of a foam material, a compressed gas, and an elastomer.

5. A device according to claim 2, wherein the device further comprises a pivot point, wherein the resistive member is coupled to the pivot point.

6. A device according to claim 1, wherein the resistive member configured to at least one of resist and provide relative movement of the first arm member is further configured to at least one of resist and provide relative movement of the first arm member with respect to the second arm member.

7. A device for flexing tissue about an arm joint of a wearer, the device comprising:
   a first member configured to couple to a first arm portion of a wearer;
   a sliding contact surface coupled to the first member and configured to translate along the first member;
   a second member configured to couple to a second arm portion of a wearer, the second member coupled to the first member at a device pivot connection; and
   a resistive member configured to at least one of resist and provide relative movement of the first member.

8. A device according to claim 7, wherein the resistive member is a spring.

9. A device according to claim 7, wherein the resistive member has resistance provided by at least one of a foam material, a compressed gas, and an elastomer.

10. A device according to claim 7, wherein the resistive member is coupled to a pivot point of the device.

11. A device according to claim 7, wherein the resistive member configured to at least one of resist and provide relative movement of the first arm member is further configured to at least one of resist and provide relative movement of the first arm member with respect to the second arm member.

12. A method of assembling a device for flexing tissue about a joint of an arm of a wearer, comprising:
   providing a first member configured to couple to a first arm portion of a wearer;
   providing a second member configured to couple to a second arm portion of a wearer and configured to slide along the first member;
   coupling the first member to the second member at a first device pivot connection; and
   coupling the first member to a drive assembly at a second device pivot connection.

13. A method according to claim 12, further comprising coupling a resistive member configured to at least one of resist and provide relative movement of the first arm member to the second arm member.

14. A method according to claim 13, wherein coupling a resistive member further comprises coupling a resistive member comprising a spring.

15. A method according to claim 13, wherein coupling a resistive member further comprises coupling a resistive member that has resistance provided by at least one of a foam material, a compressed gas, and an elastomer.

16. A method according to claim 13, wherein coupling a resistive member to the first arm member further comprises coupling a resistive member to the first arm member at the first device pivot connection.

17. A method according to claim 12, wherein providing a first member further comprises providing a first member that comprises a sliding contact surface.

18. A method according to claim 12, wherein coupling the first member to a second member further comprises coupling the first member to the second member that comprises a sliding contact surface.

* * * * *